US006569406B2

(12) United States Patent
Stevenson et al.

(10) Patent No.: US 6,569,406 B2
(45) Date of Patent: May 27, 2003

(54) INHALEABLE SPRAY DRIED 4-HELIX BUNDLE PROTEIN POWDERS HAVING MINIMIZED AGGREGATION

(75) Inventors: Cynthia Stevenson, Mountain View, CA (US); Jayne E. Hastedt, San Carlos, CA (US); S. Russ Lehrman, Los Altos, CA (US); Hi-Shi Chiang, San Jose, CA (US); David B. Bennett, San Jose, CA (US); David Lesikar, Palo Alto, CA (US); Bing Yang, Redwood City, CA (US); David Gong, San Mateo, CA (US); Kirsten Cabot, San Francisco, CA (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 09/923,519

(22) Filed: Aug. 7, 2001

(65) Prior Publication Data

US 2002/0065399 A1 May 30, 2002

Related U.S. Application Data

(60) Provisional application No. 60/223,144, filed on Aug. 7, 2000, provisional application No. 60/228,634, filed on Aug. 29, 2000, and provisional application No. 60/240,478, filed on Oct. 13, 2000.

(51) Int. Cl.[7] ............................ A61K 9/00; A61K 9/14; A61K 9/12

(52) U.S. Cl. ...................... 424/43; 46/489; 128/203.15; 514/2

(58) Field of Search ............................ 424/43, 489, 46; 514/2; 128/203.15

(56) References Cited

U.S. PATENT DOCUMENTS

| | | |
|---|---|---|
| 4,917,685 A | 4/1990 | Viswanathan et al. |
| 5,284,678 A | 2/1994 | Hirschfeld et al. |
| 5,300,317 A | 4/1994 | Ivarson |

(List continued on next page.)

FOREIGN PATENT DOCUMENTS

| | | |
|---|---|---|
| EP | 0177478 B2 | 4/1986 |
| EP | 0216485 A1 | 4/1987 |
| EP | 0303746 B2 | 2/1989 |
| WO | WO 92/00998 | 1/1992 |
| WO | WO 92/17200 | 10/1992 |
| WO | WO 93/12811 | 7/1993 |
| WO | WO 93/12812 | 7/1993 |
| WO | WO 93/13792 | 7/1993 |
| WO | WO 93/19776 | 10/1993 |
| WO | WO 96/11702 | 4/1996 |
| WO | WO 96/11703 | 4/1996 |
| WO | WO 96/11704 | 4/1996 |
| WO | WO 96/19197 | 6/1996 |
| WO | WO 96/21459 | 7/1996 |
| WO | WO 96/21460 | 7/1996 |
| WO | WO 96/21461 | 7/1996 |
| WO | WO 96/39173 | 12/1996 |
| WO | WO 97/02833 | 1/1997 |
| WO | WO 97/03692 | 2/1997 |
| WO | WO 97/39768 | 10/1997 |
| WO | WO 0000176 A | 1/2000 |
| WO | WO 0010541 * | 3/2000 |
| WO | WO 00/10541 | 3/2000 |
| WO | WO 0132144 A | 5/2001 |

OTHER PUBLICATIONS

Adler M et al., "Stability and surface activity of lactate dehydrogenase in spray–dried trehalose," J. Pharm Sci, vol. 88 (No. 2), p. 199–208, 1999.

Bell, Leonard N. et al., "Thermally Induced Denaturation of Lyophilized Bovine Somatotropin and Lysozyme as Impacted by Moisture and Excipients," Journal of Pharmaceutical Sciences, vol. 84 (No. 6), p. 707–712, Jun. 1995.

Cleland, Jeffrey L. et al., "Stable Formulations of Recombinant Human Growth Hormone and Interferon–y for Microencapsulation in Biodegradable Microspheres," Pharmaceutical Research, vol. 13 (No. 10), p. 1464–1475, 1996.

Costantino, Henry R. et al., "Effect of Excipients on the Stability and Structure of Lyophilized Recombinant Human Growth Hormone," Journal of Pharmaceutical Sciences, vol. 87 (No. 11), p. 1412–1420, Nov. 1998.

Ip, Anna Y. et al., "Stability of Recombinant Consensus Interferon to Air–Jet and Ultrasonic Nebulization," Journal of Pharmaceutical Sciences, vol. 84 (No. 10), p. 1210–1214, Oct. 1995.

Hsu, C.C. et al., "Determining the Optimum Residual Moisture in Lyophilized Protein Pharmaceuticals," Develop. Biol. Standard, vol. 74, p. 255–271, 1990.

Johnson Olufunmi L. et al., "The Stabilization and Encapsulation of Human Growth Hormone into Biodegradable Microspheres," Pharmaceutical Research, vol. 14 (No. 6), p. 730–735, 1997.

Maa Yuh–Fun et al., "Spray–Drying of Air–Liquid Interface Sensitive Recombinant Human Growth Hormone," Journal of Pharmaceutical Sciences, vol. 87 (No. 2), p. 152–159, Feb. 1998.

Mumenthaler, Marco et al., "Feasibility Study on Spray–Drying Protein Pharmaceuticals: Recombinant Human Growth Hormone and Tissue–Type Plasminogen Activator," Plenum Publishing Corporation, vol. 11 (No. 1), p. 12–20, 1994.

*Primary Examiner*—Michael G. Hartley
*Assistant Examiner*—M. Haghighatian
(74) *Attorney, Agent, or Firm*—Susan T. Evans; Felissa H. Cagan; Mark A. Wilson

(57) ABSTRACT

The present invention provides highly dispersible spray-dried powder compositions, and in particular, inhaleable dry powder compositions for aerosolized delivery to the lungs. The powders of the invention are produced by spray drying a 4 α-helix bundle protein under conditions which both (i) protect the protein from aggregation and (ii) provide particles suitable for inhalation (i.e., demonstrating superior aerosol performance).

52 Claims, No Drawings

U.S. PATENT DOCUMENTS

| | | | |
|---|---|---|---|
| 5,507,871 A | | 4/1996 | Morino et al. |
| 5,547,696 A | | 8/1996 | Sorensen |
| 5,552,385 A | | 9/1996 | Christensen et al. |
| 5,567,677 A | | 10/1996 | Castensson et al. |
| 5,582,643 A | | 12/1996 | Takei et al. |
| 5,589,167 A | | 12/1996 | Cleland et al. |
| 5,612,135 A | | 3/1997 | Matsui et al. |
| 5,612,315 A | | 3/1997 | Pikal et al. |
| 5,631,225 A | | 5/1997 | Sorensen |
| 5,641,510 A | | 6/1997 | Clark et al. |
| 5,653,996 A | | 8/1997 | Hsu |
| 5,654,010 A | | 8/1997 | Johnson et al. |
| 5,667,808 A | | 9/1997 | Johnson et al. |
| 5,705,482 A | | 1/1998 | Christensen et al. |
| 5,753,219 A | | 5/1998 | Cleland et al. |
| 5,763,394 A | | 6/1998 | O'Connor et al. |
| 5,780,599 A | | 7/1998 | Junker et al. |
| 5,804,557 A | | 9/1998 | Cleland et al. |
| 5,834,598 A | | 11/1998 | Lowman et al. |
| 5,849,535 A | | 12/1998 | Cunningham et al. |
| 5,849,700 A | | 12/1998 | Sorensen et al. |
| 5,849,704 A | | 12/1998 | Sorensen et al. |
| 5,851,992 A | | 12/1998 | Sorensen |
| 5,891,478 A | | 4/1999 | Johnson et al. |
| 5,898,030 A | | 4/1999 | Samaritani |
| 5,904,951 A | | 5/1999 | Yamanaka et al. |
| 5,952,008 A | | 9/1999 | Backstrom et al. |
| 5,977,069 A | | 11/1999 | Sorensen |
| 6,004,574 A | | 12/1999 | Backstrom et al. |
| 6,004,583 A | | 12/1999 | Plate et al. |
| 6,022,858 A | | 2/2000 | Sorensen et al. |
| 6,051,256 A | | 4/2000 | Platz et al. |
| 6,099,517 A | | 8/2000 | Daugherty |
| 6,191,107 B1 | | 2/2001 | Yamagata et al. |
| 6,197,369 B1 | | 3/2001 | Watano et al. |
| 6,372,258 B1 | * | 4/2002 | Platz et al. ................. 424/489 |

OTHER PUBLICATIONS

Niven, Ralph W. et al., "Protein Nebulization II. Stability of G–CSF to Air–Jet Nebulization and the Role of Protectants," International Journal of Pharmaceutics, p. 191–201, 1996.

Niven, Ralph W. et al., "Some Factors Associated with the Ultrasonic Nebulization of Proteins," Pharmaceutical Research, vol. 12 (No. 1), p. 53–59, 1995.

O'Hagan, Derek T. et al., "Nasal Absorption Enhances for Biosynthetic Human Growth Hormone in Rats ," Pharmaceutical Research, vol. 7 (No. 7), p. 772–776, 1990.

Tzannis, Stelios T. et al., "Irreversible Inactivation of Interleukin 2 in a Pump–Based Delivery Environment," Proc. Natl. Acad. Sci., p. 5460–5465, May 1996.

Zhang, Mei Z. et al., "The Effect of the Reconstitution Medium on Aggregation of Lyophilized Recombinant Interleukin–2 and Ribonuclease A," Pharmaceutical Research, vol. 13 (No. 4), p. 643–646, 1996.

* cited by examiner

INHALEABLE SPRAY DRIED 4-HELIX BUNDLE PROTEIN POWDERS HAVING MINIMIZED AGGREGATION

CROSS REFERENCE TO RELATED APPLICATIONS

This application claims the benefit of priority of the following U.S. provisional applications: Patent Application Ser. No. 60/223,144, filed Aug. 7, 2000; Patent Application Ser. No. 60/228,634, filed Aug. 29, 2000; and Patent Application Ser. No. 60/240,478, filed Oct. 13, 2000, the contents of which are incorporated herein by reference in their entirety.

FIELD OF THE INVENTION

The present invention is directed to highly dispersible spray-dried powder compositions, and in particular, to inhaleable dry powder compositions for aerosolized delivery to the lungs. The powders of the invention are produced by spray drying a 4 α-helix bundle protein under conditions which both (i) protect the protein from aggregation and (ii) provide particles ideally suited for inhalation (i.e., demonstrating superior aerosol performance).

BACKGROUND OF THE INVENTION

Traditionally, inhalation therapy has played a relatively minor role in the administration of biotherapeutics and conventional pharmaceuticals when compared to more traditional drug administration routes, such as oral and intraveneous. Injection is still the customary route of delivery of biotherapeutics (e.g., peptides, proteins and nucleic acids), and due to the many drawbacks associated with injection (e.g., inconvenience, discomfort, patient aversion to needle-based delivery methods), alternative administration routes are needed.

Pulmonary delivery is one such alternative administration route which can offer several advantages over needle-based administration. These advantages include the convenience of patient self-administration, the potential for reduced drug side-effects, ease of delivery by inhalation, the elimination of needles, and the like. Many preclinical and clinical studies with inhaled proteins, peptides, DNA and small molecules have demonstrated that efficacy can be achieved both within the lungs and systemically. However, despite such results, the role of inhalation therapy in the health care field has not grown as expected over recent years, in part due to a set of problems unique to the development of inhaleable drug formulations. In particular, dry powder formulations for pulmonary delivery, while offering unique advantages over cumbersome liquid dosage forms and propellant-driven formulations, can be prone to aggregation and low flowability phenomena which considerably diminish the efficiency of dry powder-based inhalation therapies.

In recent years, driven in part by the interest in aerosol delivery of dry powders and some of the short-comings of well-known techniques for preparing dry powders (e.g., lyophilization, air-drying, and co-precipitation), spray drying has been employed as a method for preparing micron-sized powders for pulmonary administration (Platz, R., et al., International Patent Publication No. WO 96/32149). Spray drying utilizes a hot gas stream to evaporate micro-dispersed droplets created by atomization of a liquid feedstock to form dry powders. While spray-drying has been long employed in the food and pharmaceutical industries to prepare dry powders, its application to therapeutic proteins has been rather limited because of the concern that certain proteins may be thermally degraded during the spray drying process. While there is now a growing body of evidence to support the general utility of spray drying macromolecule-based biotherapeutic formulations to produce biologically active powders suitable for inhalation (Foster, L., et al., International Patent Publication No. WO 98/16205; Platz, R., et al., International Patent Publication No. WO 97/41833; Eljamal, M., et al., International Patent Publication No. WO 96/32152; Eljamal, M., et al., International Patent Publication No. 96/32116; Eljamal, M., et al., International Patent Publication No. 95/24183; Bennett, D., et al., International Patent Publication No. 01/00312), many peptides and proteins, when exposed to the harsh conditions of spray drying, are prone to a certain degree of aggregation (unfolding).

Certain proteins, and in particular, proteins characterized as belonging to the 4-α-helical bundle superfamily (e.g., hGH, INF-γ, INF-β, GM-CSF, M-CSF, IL-2, IL-4, IL-5) are extremely susceptible to denaturation, unfolding, aggregation and precipitation, with loss of biological activity. These proteins share extensive sequence and structural (conformational) homology, characterized by a protein core folded in an up, up, down, down, antiparallel, left handed for α-helix bundle with a double-overhand loop topology. Thus, due to their instability, spray-drying and formulating this class of proteins for inhalation presents a unique set of challenges.

Several aspects of the spray-drying process can contribute to protein unfolding for this class of proteins, such as shear stress, high temperatures, exposure of a protein in a droplet to the liquid air interface (surface effects), liquid-wall interactions, and the like, and can result in the formation of dried particles which contain a high degree of protein in aggregated form that are in a size range unsuitable (or at least non-optimal) for inhalation. Examples of 4-α-helix bundle protein instability upon processing are numerous. Recombinant consensus α-inferferon (rConIFN) was shown to be destabilized by air-jet nebulization, which resulted in rapid formulation of insoluble noncovalent aggregates, with only about 25% of the initial monomeric protein remaining after 25 minutes of nebulization. (Ip, A. Y., et al., *J. Pharm Sci.,* 84(10), 1995: 1210–1214). In an examination of the feasibility of spray-drying proteins such as hGH, 25% of the protein was found to be degraded during processing, although addition of 0.1% (w/v) polysorbate 20 reduced the formation of insoluble and soluble aggregates during spray drying by about 70–85% (Mumenthaler, M., et al., *Pharm. Research,* 11 (1), 1994: 12). The addition of polysorbate 20 in the presence of divalent zinc ions was found to further suppress hGH degradation upon spray-drying (Maa, Y-F., et al., *J. Pharm. Sci.,* 87 (2), 1998: 152–159). In an investigation of the bioactivity and physical stability of interleukin-2 upon delivery by continuous infusion, transient surface association of IL-2 with the catheter tubing was identified as being responsible for the majority of the biological activity loss observed (~90% loss) (Tzannis, S., et al., *Proc. Natl. Acad. Sci. USA,* 93: 5460 (1996).

Of the 4-α-helix bundle proteins, growth hormone is particularly unstable, and many approaches have been employed to date to arrive at stable therapeutic formulations. Degradation products of growth hormone include deamidated or sulfoxylated products and dimer or polymer forms. Specifically, the predominant degradation reactions of growth hormone are (i) deamidation by direct hydrolysis or via a cyclic succinimide intermediate to form various amounts of L-asp-hGH, L-iso-asp-hGH, D-asp-hGH, and D-iso-asp-hGH, and (ii) oxidation of the methionine residues in positions 14 and 125. Human growth hormone is also readily oxidized in positions 14 and 125. More importantly, aggregate formation in human growth hormone is detrimental, since this can lead to reduced bioactivity and increased immunogenicity (Becker, et al., *Biotech. AppL Biochem.,* 9:478–487 (1987); Leppert, P., Moore, W. V., *J. Clin. Endocrinol.,* 51: 691–697 (1980)).

Thus, protein denaturation, the formation of aggregates, and production of powders having poor flow properties and low dispersibilities continue to plague development efforts to prepare aerosolizable 4-helix bundle protein powders for inhalation therapy. Moreover, many of the approaches utilized to date are undesirable or unsuited for powder formulations for inhalation therapies, such as the use of surfactants, which are thought to interfere with the lung pathology and are epithelial irritants, or increasing the protein solids concentration of pre-spray dried solutions, which can result in particles that are too big for efficient delivery to the deep lung.

Thus, a need exists for improved inhaleable powder aerosols for the pulmonary delivery of 4-helix bundle proteins, and in particular, for spray-dried powders having excellent aerosol properties and reduced aggregation.

SUMMARY OF THE INVENTION

The present invention is based upon the discovery of unique conditions for spray drying 4-α helix bundle proteins to provide respirable protein powder formulations, and in particular, 4 α-helix bundle protein powder formulations that are (i) resistant to protein aggregation during spray drying and upon storage, (ii) highly dispersible, and (iii) in a size range suitable for inhalation. The stabilizing conditions or excipients employed are effective to mask the protein from the extreme conditions of spray drying, such that process parameters which would otherwise (i.e., in the absence of such stabilizing conditions) lead to a large degree of protein aggregation are suitable, and often optimal, for forming particles (i) containing less than 10% total protein aggregates, and more preferably less than 7% total aggregates, and even more preferably less than 5% total aggregates, and (ii) having an emitted dose of at least about 65%, and more preferably of at least about 70%. The spray dried particles of the invention are sized appropriately for inhalation therapy, i.e., having an MMAD less than 10 microns, preferably less than 5 microns, more preferably less than 3.5 microns, and most preferably less than 3 microns.

In a preferred embodiment of the invention, the 4-α helix bundle protein comprises human growth hormone.

The spray dried formulations of the invention, in certain particular embodiments, include a stabilizing excipient effective to maintain or lower the aggregate level (i.e., either the insoluble or soluble aggregate level) of the powder in comparison to the spray-dried neat formulation. Specifically, stabilizing excipients include sugars, amino acids, and oligomers comprising 2 to 5 amino acids.

In one embodiment, the stabilizing excipient is sucrose or raffinose.

In another embodiment, the stabilizing excipient is leucine, isoleucine, or norleucine.

In yet another embodiment, the stabilizing excipient is trileucine.

In one particular embodiment of the invention, the stabilizer is present in the spray dried particles in an amount less than or equal to about 30% by weight.

In yet another particular embodiment, the spray dried powder of the invention comprises at least about 50% by weight of a 4 α-helical bundle protein such as human growth hormone.

The spray dried powder of the invention is also stable upon storage, such that, in a certain embodiment, it maintains a total aggregate content of less than about 10% after storage for one month at 40° C.

In yet another embodiment of the invention, the 4 α-helical bundle protein is spray dried under optimized spray drying conditions such that the presence of additional stabilizers is not required. Surprisingly, the neat spray drying methodology is effective to produce spray dried particles containing minimal amounts (i.e., less than 10%) of protein aggregates (soluble and insoluble aggregates), excellent dispersibilities (greater than 65%, and preferably 70% emitted dose), and small aerodynamic particle sizes (MMADs less than about 4 microns).

In another aspect, the invention provides formulations and spray-drying conditions which minimize spray-drying induced changes in secondary structure of the 4 α-helical bundle protein, i.e., the α-helix is largely retained. In particular, the invention provides spray dried powders which exhibit a loss in α-helix of no more than about 50%, preferably no more than 40%, more preferably no more than 30%, and even more preferably no more than about 10–20% relative to the native structure prior to spray-drying, as measured by either FT IR or circular dichroism (CD). Particularly preferred conformational stabilizers and solvents for use in the spray-dried formulations of the invention are those which preserve α-helix content of the protein and disfavor 3-sheet formation including alcohols, in particular, ethanol. In one embodiment of this aspect of the invention for preserving α-helicity of the protein, the solids concentration in the pre-spray dried solution is less than 2 mg/mL.

These and other objects and features of the invention will become more fully apparent when the following detailed description is read in conjunction with the accompanying examples.

DETAILED DESCRIPTION OF THE INVENTION

I. Definitions

The following terms as used herein have the meanings indicated.

As used herein, growth hormone may be growth hormone from any origin such as avian, bovine, equine, human, ovine, and porcine, with human growth hormone being most preferred. For protein active agents, e.g., any of the 4 α-helical bundle proteins described herein, the invention contemplates the use of natural and synthetically or recombinantly-derived proteins, as well as analogs thereof, to the extent that they retain a reasonable degree of therapeutic activity associated with full length peptide/protein.

As used herein, the term "analog" refers to proteins in which one or more amino acids have been substituted, deleted (i.e., fragments), added (e.g., derivatives having an N- or C-terminal extension such as Met-hGH), or otherwise modified from the native (wild-type) human sequence, and which exhibits at least about 10, 20, 30, or 40%, and preferably at least 50%, 60%, or 70%, and most preferably at least 80%, 90%, 95%, 100% or greater than 100% bioactivity of that of the native (non-synthetic), endogenous peptide.

"Amino acid" refers to any compound containing both an amino group and a carboxylic acid group. Although the amino group most commonly occurs at the position adjacent to the carboxy function, the amino group may be positioned at any location within the molecule. The amino acid may also contain additional functional groups, such as amino, thio, carboxyl, carboxamide, imidazole, etc. An amino acid may be synthetic or naturally occurring, and may be used in either its racemic or optically active (D-, or L-) forms, including various ratios of stereoisomers.

"Leucine" is meant to encompass D-leucine, L-leucine, racemic leucine, and various ratios of the two enantiomers.

A "neat" formulation in accordance with the invention refers to a spray dried powder that contains a 4-α helix protein and optionally a buffer (typically from 0–15% by weight of the dry powder), that is substantially absent additional excipients, i.e., contains less than about 1% by weight additional excipients.

"Peptides" are composed of less than about 100 amino acids each joined by a peptide bond. Peptides can be homo- or hetero-peptides (i.e., composed of identical or different amino acid residues as defined above), and can vary in length from two amino acids to about one hundred amino acids "Dipeptide", also referred to herein as a dimer, refers to a peptide composed of two amino acids joined by a peptide bond.

"Tripeptide", also referred to herein as a trimer, refers to a peptide composed of three amino acids.

A "protein" is a macromolecule composed of 100 amino acids or greater.

"Total protein aggregates" refers to the percentage of soluble and insoluble protein aggregates relative to 100% monomeric 4-α helix protein, determined by size exclusion chromatography and UV spectroscopy, respectively.

"Aggregate level" refers to either soluble or insoluble aggregates unless otherwise indicated.

A "surface active" material is one having surface activity (measured, e.g., by surface tensiometry), as characterized by its ability to reduce the surface tension of the liquid in which it is dissolved. Surface tension, which is associated with the interface between a liquid and another phase, is that property of a liquid by virtue of which the surface molecules exhibit an inward attraction.

A "rapid acting" dry powder is a powder that does not possess controlled or sustained release characteristics when administered by inhalation.

As used herein, "aqueous solvent" refers to water or a mixed solvent system comprising water and one or more water-miscible co-solvents.

"Dry powder" refers to a powder composition that typically contains less than about 10% moisture, preferably less than 7% moisture, more preferably contains less than about 5–6% moisture, and even more preferably contains less than about 3% moisture, and most preferably contains less than 2% moisture, depending upon the type of active agent in the powdered composition.

An "inhaleable" dry powder that is "suitable for pulmonary delivery" refers to a composition comprising solid (i.e., non-solution) particles that are capable of (i) being readily dispersed in or by an inhalation device and (ii) inhaled by a subject so that at least a portion of the particles reach the lungs to permit penetration into the alveoli. Such a powder is considered to be "respirable" or "inhaleable".

"Aerosolized" particles are particles which, when dispensed into a gas stream by either a passive or an active inhalation device, remain suspended in the gas for an amount of time sufficient for at least a portion of the particles to be inhaled by the patient, so that a portion of the inhaled particles reaches the lungs.

"Emitted Dose" or "ED" provides an indication of the delivery of a drug formulation from a suitable inhaler device after a firing or dispersion event. More specifically, for dry powder formulations, the ED is a measure of the percentage of powder which is drawn out of a unit dose package and which exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-determined parameter, and is typically determined using an in-vitro device set up which mimics patient dosing. To determine an ED value, a nominal dose of dry powder, typically in unit dose form, is placed into a suitable dry powder inhaler (such as that described in U.S. Pat. No. 5,785,049, assigned to Inhale Therapeutic Systems) which is then actuated, dispersing the powder. The resulting aerosol cloud is then drawn by vacuum from the device, where it is captured on a tared filter attached to the device mouthpiece. The amount of powder that reaches the filter constitutes the emitted dose. For example, for a 5 mg dry powder-containing dosage form placed into an inhalation device, if dispersion of the powder results in the recovery of 4 mg of powder on a tared filter as described above, then the emitted dose for the dry powder composition is: 4 mg (delivered dose)/5 mg (nominal dose)×100=80%. For non-homogenous powders, ED values provide an indication of the delivery of drug from an inhaler device after firing rather than of dry powder, and are based on amount of drug rather than on total powder weight. Similarly for MDI dosage forms, the ED corresponds to the percentage of drug which is drawn from a dosage form and which exits the mouthpiece of an inhaler device.

"Free from surfactant" in the context of the present invention refers to a spray dried powder comprising less than about 0.1% by weight of a surfactant.

"Fine Particle Dose" (FPD3.$_{3}$ μm) provides a measure of aerosol quality and is defined as the amount of powder which is under 3.3 microns ($FPD_{<3.3\ \mu m}$) determined by cascade impaction. This parameter corresponds to the total mass under stage 3 of an Andersen impactor when operated at a flow rate of 1 cfm (28.3 L/min) and provides an in vitro estimate of the dose below 3.3 microns delivered to the patient.

"Fine particle fraction" ($FPF_{<3.3\ \mu m}$) provides a meaure of aerosolized powder delivery efficiency from a unit dosage form (e.g., a blister pack) to the deep lung, and is determined experimentally using a short stack Anderson cascade impactor operated at a vacuum of 28.3 liters per minute. The FPF is defined as the total mass, in milligrams, of aerosolized powder having a particle size less than 3.3 micrometers, relative to the mass of powder contained in a unit dosage form, in milligrams, and expressed as a percentage.

A "dispersible" or "aerosolizable" powder is one having an ED value of at least about 30%, more preferably 40–50%, and even more preferably at least about 50–60% or greater. A powder having superior aerosolizability possesses an ED value of at least about 65% or greater.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size (e.g., electron microscopy, light scattering, laser diffraction).

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, in air, as the particle. The aerodynamic diameter encompasses particle shape, density and physical size of a particle. As used herein, MMAD refers to the midpoint or median of the aerodynamic particle size distribution of an aerosolized powder determined by cascade impaction, unless otherwise indicated.

"Pharmaceutically acceptable salt" includes, but is not limited to, salts prepared with inorganic acids, such as chloride, sulfate, phosphate, diphosphate, bromide, and nitrate salts, or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, lithium, sodium, potassium, barium, calcium, aluminum, and ammonium (including alkyl substituted ammonium).

"Pharmaceutically acceptable excipient or carrier" refers to an excipient that may optionally be included in the compositions of the invention, and taken into the lungs with no significant adverse toxicological effects to the subject, and particularly to the lungs of the subject.

"Pharmacologically effective amount" or "physiologically effective amount" is the amount of a 4-α helix bundle protein present in a particulate dry powder composition as described herein that is needed to provide a desired level of protein in the bloodstream of a subject to be treated to give an anticipated physiological response when such composition is administered pulmonarily. The precise amount will depend upon numerous factors, e.g., the 4-α helix bundle protein, the activity of the composition, the particular inhaler device employed, the physical characteristics of the powder, intended patient use (i.e., the number of doses administered per day), patient considerations, and the like, and can readily be determined by one skilled in the art, based upon the information provided herein.

II. Formulation Components

The present invention is based in part upon the Applicants' discovery of optimal conditions for spray drying molecules, and in particular proteins such as 4 α-helical bundle proteins, to prepare stable, non-aggregated respirable dry powders. The challenge facing the inventors was to balance the factors influencing protein aggregation, deamidation (degradation), and denaturation with those affecting aerodynamic particle size and particle dispersibility, as well as storage stability. These factors often work in opposing directions, such that conditions which provide minimized protein aggregation often result in particles having properties that are unsuitable for inhalation (e.g., large particle sizes, low dispersibilities).

Described below are preferred stabilizing excipients and formulation components, which, when employed in conjunction with particular spray drying process parameters described in greater detail below, are effective to mask/shield the protein from the harsh conditions of spray drying, such that conditions which would otherwise lead to a large degree of protein aggregation are suitable, and often optimal for forming respirable particles. Not to be bound by any particular theory, the stabilizer may work in a variety of ways, e.g., by decreasing surface tension, increasing diffusion, hydrophobic/ionic association with the protein to stabilize against unfolding, buffering, etc. Thus, these stabilizers can be employed to not only minimize protein aggregation, but to increase the aerosol performance of the resulting spray-dried compositions, and in some cases, to provide aerosolizable formulations in situations where an aerosolizable formulation, and in particular an aerosolizable 4 α-helical bundle protein formulation, was previously unknown or unattainable.

The components of the spray-dried compositions of the invention will now be described.

A. 4 α-Helical Bundle Proteins

The present invention is directed but not limited to protein pharmaceutical agents and in particular, to 4 α-helical bundle proteins. Proteins belonging to this structural family include G-CSF, growth hormone, IFN-γ, IFN-β, GM-CSF, IL-2, IL-4, IL-5, and M-CSF. Although having limited homology at the sequence level, these growth factors and cytokines share a four helix topology (A-D) with overhand loop connections. More specifically, these proteins share a common fold in their conformational structure, characterized by an up-up-down-down, antiparallel, left-handed, four-α-helical bundle with a double overhand loop topology. One illustrative 4 α-helical protein, IL-2, in its native structure possesses from about 42–63% a helix, with little or no β-sheets (Tzannis, S., et al., *Proc. Natl. Acad. Sci. USA,* 93:5460–5465 (1996). One of the aims of the present invention is to produce respirable protein powders in which the protein α-helix secondary structure is retained while β-sheet formation is inhibited during spray drying.

Particularly suitable for use in the methods and compositions described herein are growth factors such as growth hormone, and in particular human growth hormone. Human growth hormone (hGH) is a protein secreted from the anterior pituitary gland in a pulsatile manner and is essential for regulation of growth. hGH is a single chain polypeptide of 191 amino acids with a molecular weight of approximately 22 kDa and a pI near 5.3. hGH stimulates skeletal growth throughout life and is essential in the normal metabolism of body nutrients, carbohydrates, proteins and lipids. It plays an important role in protein metabolism as it tends to increase protein synthesis (anabolism) and decreases protein destruction (catabolism) by using fat as a more efficient source of energy. The amount of natural hGH secreted is high in children, reaches maximal levels during adolescence and then decreases to its lowest levels during adulthood. Human growth hormone for use in the compositions of the invention will typically be recombinantly prepared (e.g., by *E. coli*) or pituitary-derived.

The amount of 4 α-helical bundle protein in the formulation will be that amount necessary to deliver a therapeutically effective amount of the protein per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active protein, typically from about 2% to about 95% by weight active protein, and more typically from about 5% to 85% by weight 4-α helix bundle protein, and will also depend upon the relative amounts of excipients/additives contained in the composition. More specifically, the spray dried composition will typically contain at least about one of the following percentages of active agent: 10%, 20%, 30%, 40%, 50% or more by weight of 4-α helix bundle protein. Preferably, the spray dried powder will contain at least about 50%, e.g., from about 50–100% by weight 4-α helix bundle protein such as human growth hormone. In specific embodiments of the invention, the spray dried powder will comprise at least about 60% by weight 4-α helix bundle protein, even more preferably at least about 70% by weight 4-αhelix bundle protein (e.g., from about 70%–100% active protein), more preferably at least about 80% or more by weight 4-α helix bundle protein (80–100% by weight active protein), or from about 90–100% by weight 4-α helix bundle protein. In general, a high protein content is desired in the particles. The spray-dried compositions of the invention are particularly useful for proteins, e.g., 4-α helix bundle proteins, that are delivered in doses of from 0.001 mg/day to 100 mg/day, preferably in doses from 0.01 mg/day to 75 mg/day, and more preferably in doses from 0.10 mg/day to 50 mg/day.

B. Stability-enhancing Excipients

Compositions of the invention will, in some instances, include one or more protective or stabilizing excipients. As discussed above, one aspect of the invention is based upon the Applicants' discovery that when employed in conjunction with optimized spray-drying conditions, certain excipients or additives (e.g., amino acids such as leucine, oligomers such as trileucine, sugars such as sucrose, mannitol, and raffinose, and salts such as sodium chloride, potassium chloride, and the like) are superior not only in their ability to minimize protein aggregation, but to also reduce the aerodynamic size and increase the dispersibility of the resulting powdered compositions, as demonstrated in the Examples using the exemplary protein, human growth hormone (hGH). Moreover, several of the exemplary compositions of the invention were stable upon extended storage, i.e., having aggregate levels that did not increase substantially upon storage.

Exemplary stabilizers include amino acids, peptides and particularly oligomers comprising 2–9 amino acids, and more preferably 2–5 mers, and polypeptides, all of which may be homo or hetero species. Amino acids for use as 4 α-helical bundle protein stabilizers include glycine (gly), alanine (ala), valine (val), norvaline (2-aminopentanoic acid), 2-aminoheptanoic acid, leucine (leu), isoleucine (ile), methionine (met), proline (pro), phenylalanine (phe), tryptophan (trp), serine (ser), threonine (thr), cysteine (cys), tyrosine (tyr), asparagine (asp), glutamic acid (glu), lysine (lys), arginine (arg), histidine (his), norleucine (nor), and modified forms thereof Preferred are amino acids such as leucine, isoleucine, norleucine, valine, norvaline, 2-aminoheptanoic acid, phenylalanine, and tryptophan. Particularly preferred stabilizing amino acids/excipients are leucine, isoleucine, and norleucine.

In considering the characteristics of preferred amino acid stabilizers, preferable are those amino acids having relatively low solubilities in water, e.g., from about 10 mg/ml to about 75 mg/ml. Not to be bound by any theory, reduced aqueous solubility lends to decreasing moisture sorption and delayed crystallization in the resulting spray dried powder, both of which are desirable characteristics for a respirable powder of the invention (e.g., in this regard, leucine is preferred over histidine which is preferred over alanine which is preferred over glycine). Also preferred are amino acids having somewhat large Van der Waals volumes, e.g., greater than about 100 $A^3$, e.g., isoleucine, leucine, lysine, methionine and phenylalanine. Increasing Van der Waals volume tends to correlate with increased Tg of the resulting spray dried pharmaceutical powder, thus indicating greater storage stability. Also preferred are hydrophobic amino acids, such as leucine (leu), valine (val), isoleucine (isoleu), tryptophan (try), alanine (ala), methionine (met), phenylalanine (phe), tyrosine (tyr), histidine (his), and proline (pro). Another factor preferred for an amino acid stabilizer is the ability to decrease the surface tension of water, which correlates with lower MMDs and reduced protein aggregation in the resulting spray dried particles; surface active amino acids which are effective in lowering the surface tension of water include asparagine, isoleucine, phenylalanine, tryptophan, tyrosine, leucine and valine. Also preferred are amino acids having a glass transition temperature greater than 40° C., more preferably greater than 50° C., even more preferably greater than 60° C., and most preferably 70° C. or greater. The inclusion of such amino acids in spray dried powders typically improves the aerosol performance, and in particular, MMADs and EDs, by about 10–25%. One particularly preferred amino acid is leucine, which due to its surface activity, tends to concentrate on the surface of spray-dried particles, i.e., the concentration of leucine on the surface of spray dried protein particles is typically greater than in the bulk powder. Other surface active amino acids which tend to concentrate on the surface of spray dried protein particles include asparagine, isoleucine, phenylalanine, tryptophan, tyrosine, norleucine and valine. This respresents another preferred feature of a stabilizer of the invention—the tendency to protect or mask the pharmaceutical agent, e.g., 4-α helical protein, during spray drying. In this particular embodiment, the pharmaceutical agent is shielded from the harsh conditions of spray drying by the presence of stabilizer molecules on the droplet surface. In this instance, the stabilizer is not an encapsulating agent and does not form a discrete coating, but rather simply accumulates at greater concentrations on the surface of the droplet during spray drying, resulting in particles having an enhanced surface concentration of stabilizer.

Also preferred for use as stabilizers are di- and tripeptides containing two or more leucyl residues, as described in Inhale Therapeutic System's International patent publication, WO 01/32144, incorporated herein by reference in its entirety. Representative of this class of stabilizer are dileucine and trileucine. A di-leucyl containing trimer may contain the two leucyl residues adjacent to each other (at the 1 and 2 positions), or they can form the ends of the trimer (occupying positions 1 and 3). The remaining amino acid contained in the trimer can be any amino acid as defined in section I above. Suitable are amino acids such as glycine (gly), alanine (ala), valine (val), leucine (leu), isoleucine (ile), methionine (met), proline (pro), phenylalanine (phe), trytophan (trp), serine (ser), threonine (thr), cysteine (cys), tyrosine (tyr), asparagine (asp), glutamic acid (glu), lysine (lys), arginine (arg), histidine (his), norleucine (nor), and modified forms thereof Preferably, for di-leucyl containing trimers, the third amino acid component of the trimer is one of the following: leucine (leu), valine (val), isoleucine (ile), tryptophan (trp) alanine (ala), methionine (met), phenylalanine (phe), tyrosine (tyr), histidine (his), and proline (pro). Exemplary trimers for use in the invention include but are not limited to the following: leu-leu-gly, leu-leu-ala, leu-leu-val, leu-leu-leu, leu-leu-ile, leu-leu-met, leu-leu-pro, leu-leu-phe, leu-leu-trp, leu-leu-ser, leu-leu-thr, leu-leu-cys, leu-leu-tyr, leu-leu-asp, leu-leu-glu, leu-leu-lys, leu-leu-arg, leu-leu-his, leu-leu-nor, leu-gly-leu, leu-ala-leu, leu-val-leu, leu-ile-leu, leu-met-leu, leu-pro-leu, leu-phe-leu, leu-trp-leu, leu-ser-leu, leu-thr-leu, leu-cys-leu, leu-tyr-leu, leu-asp-leu, leu-glu-leu, leu-lys-leu, leu-arg-leu, leu-his-leu, and leu-nor-leu.

Dimers and trimers composed of any combination of the above described amino acids are also suitable for use in the invention. Most preferred are dimers and trimers containing at least two of the following amino acids: leucine, isoleucine, valine, norleucine, phenylalanine, and tryptophan.

Although less preferred due to their limited solubility in water, additional stability and aerosol performance-enhancing peptides for use in the invention are 4-mers and 5-mers containing any combination of amino acids as described above. More preferably, the 4-mer or 5-mer will comprise two or more leucine residues. The leucine residues may occupy any position within the peptide, while the remaining (i.e., non-leucyl) amino acids positions are occupied by any amino acid as described above, provided that the resulting 4-mer or 5-mer has a solubility in water of at least about 1 mg/ml. Preferably, the non-leucyl amino acids in a 4-mer or 5-mer are hydrophilic amino acids such as lysine, to thereby increase the solubility of the peptide in water.

Also preferred are di- and tripeptides having a glass transition temperature greater than about 40° C., more preferably greater than 50° C., even more preferably greater than 60° C., and most preferably greater than 70° C.

Polyamino acids, and in particular, those comprising any of the herein described amino acids, are also suitable for use as stabilizers. Preferred are polyamino acids such as polylysine, poly-glutamic acid, and poly(lys, ala).

Also suitable for use in protecting the protein during spray drying are carbohydrate excipients carbohydrates (e.g., sugars, derivatized sugars such as alditols, aldonic acids, esterified sugars, and sugar polymers), and in particular, sugars. Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like. Preferred are non-reducing sugars, sugars that can form an amorphous or glassy phase with protein in a spray-dried solid, and sugars possessing relatively high Tgs, e.g., Tgs greater than 40° C., preferably greater than 50° C., more preferably greater than 60° C., and even more preferably greater than 70° C., and most preferably having Tgs of 80° C. and above. Particularly preferred as stabilizing excipients are sucrose, mannitol and trehalose, as can be seen from the Examples.

Also beneficial in spray drying 4-α helical proteins are electrolytes, preferably strong electrolytes. In preliminary investigations carried out by the Applicants, it has been discovered that the incorporation of electrolytes (e.g., any of a number of pharmaceutically acceptable inorganic salts such as sodium chloride, potassium chloride, sodium sulfate, potassium nitrate, and the like) into a liquid formulation containing a 4-α helical protein, to adjust the ionic strength of the solution, is also effective to "mask" the protein during spray drying. Without being bound by any theory, it is postulated that due to an increased concentration of electrolytes in solution, the ions tend to concentrate on the droplet surface during spray drying, thereby protecting or shielding the active protein in the droplet core during the spray drying process.

Additional excipients and additives useful in the present compositions and methods are provided in Inhale Therapeutic Systems' International Publication No. WO 96/32096 and in the "*Handbook of Pharmaceutical Excipients*" Third Ed., Kibbe, A. H. Editor (2000). Preferred are excipients having glass transition temperatures (Tg), above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. The compositions of the invention may also include a buffer or a pH adjusting agent, typically but not necessarily a salt prepared from an organic acid or base. Representative buffers include organic acid salts of citric acid, ascorbic acid, gluconic acid, carbonic acid, tartaric acid, succinic acid, acetic acid, or phthalic acid. Other suitable buffers include Tris, tromethamine hydrochloride, borate, glycerol phosphate and phosphate. Amino acids such as glycine are also suitable.

The spray-dried compositions of the invention are typically considered to be rapid-acting, i.e., they do not exhibit controlled or sustained release characteristics when administered by inhalation. In general, the compositions of the invention are non-microspherical and non-liposomal, and the particles tend to be non-hollow. Moreover, the spray-dried human growth hormone particles of the invention are absent surfactant, which was shown in the model protein, lactate dehydrogenase, to have a deleterious effect on storage stability of the spray-dried product (Adler, M.; Lee, G., *J. Pharm Sci: Feb* 88(2): 199–208 (1999)). Surprisingly, the Applicants have produced non-aggregated spray dried powders of human growth hormone in the absence of surfactant, which in a previous study, was shown to be essential for the prevention of protein aggregation during spray (Maa, Y-F., et al., *J. Pharm Sci,* 87(2):152–159 (1998)).

The compositions may further include flavoring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80", and pluronics such as F68 and F88, available from BASF, although at levels less than about 0.1% by weight), sorbitan esters, lipids (e.g., phospholipids such as lecithin and other phosphatidylcholines, phosphatidylethanolamines, although preferably not in liposomal form), fatty acids and fatty esters, steroids (e.g., cholesterol), and chelating agents (e.g., EDTA, zinc and other such suitable cations). When employed in a 4-α helical protein powder, pluronics are typically present in percentages below about 1% by weight and more preferably at percentages below about 0.1% by weight. One preferred excipient combination of the invention comprises a pluronic such as F68 and trileucine. Preferred cations for use in the compositions and methods of the invention include aluminum, manganese, calcium, zinc, and magnesium. Such cations, when present, are typically present in relative molar amounts ranging from about 50:1 cation (mol)/protein (mol) to about 1:1, and are more preferably between about 20:1 and 2:1. Particularly preferred are compositions containing molar ratios of cation to protein of about 2:1, 7:1, 10:1, 15:1, and 20:1. Especially preferred at these ratios is the cation, zinc, although spray-dried formulations having insignificant levels of soluble aggregates were achieved even in the absence of zinc or other divalent cations. Preferably, the composition is absent permeation enhancers, or if present, such enhancers are typically present in small quantitities, e.g., less than about 10% or so by weight, and more preferably less than about 5% by weight in the dried solid. Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998).

Generally, the pharmaceutical compositions of the invention will contain from about 1% to about 99% by weight stabilizer, preferably from about 5%–98% by weight stabilizer, more preferably from about 15–95% by weight stabilizer. Even more preferably, the spray dried composition will contain from about 0–40% by weight stabilizer, more preferably from 0–30% by weight stabilizer, e.g., preferred compositions will contain any ofthe following amounts: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% by weight stabilizer. In general, a high protein concentration is desired in the spray dried particles, and in particular for spray dried human growth hormone. Thus, the stabilizers of the invention are typically very effective in protecting the protein during spray drying, since they are ideally present at concentrations of less than about 30% by weight (solids). Typically, the optimal amount of stabilizer is determined experimentally, i.e., by preparing compositions containing varying amounts of stabilizer (ranging from low to high), examining the protein aggregation, MMADs and dispersibilities of the resulting spray-dried compositions, and then further exploring the range at which optimal aerosol performance is attained with no significant adverse effect upon protein aggregation or storage stability.

III. Preparing Dry Powders

The dry powder formulations of the invention are prepared by spray drying under conditions which minimize the extent of protein aggregation. Spray drying of the formulations is carried out, for example, as described generally in the "Spray Drying Handbook", $_5$th ed., K. Masters, John Wiley & Sons, Inc., NY, N.Y. (1991), and in Platz, R., et al., International Patent Publication Nos. WO 97/41833 (1997) and WO 96/32149 (1996), the contents of which are incorporated herein by reference.

The pharmaceutical agent, preferably a 4 α-helical protein such as a growth hormone, is typically spray dried from an aqueous solution or suspension, depending upon the solubility of the active protein at the pH range employed. Utilizing this approach, the 4-α helix bundle protein is first dissolved or suspended in water, optionally containing a physiologically acceptable buffer. In a preferred embodiment, the protein (e.g. hGH) is dissolved in an aqueous solution. The pH range of active agent-containing solutions is generally between about 3 and 11, more typically between about 3.5–9, with nearer neutral pHs being preferred in some instances (5.5–7.8), since such pHs may aid in maintaining the physiological compatibility of the powder after dissolution of powder within the lung. The solution is thus prepared at pHs that are at, above or below the pI of the protein. That is to say, the liquid formulation is spray dried at a pH ranging from about 3–4, 4–5, 5–6, 6–7, 7–8, or 8–9. As shown in by the Examples herein, surprisingly superior aerosol properties were obtained for hGH powders spray dried at low pH conditions, i.e., at pHs below about 4 (from 3.5–4). However, suitable powders were also obtained when spray dried at near neutral pHs (7–8). In one embodiment of the invention, a suspension of a 4-α helical protein such as hGH is spray dried at a pH that is about equal to its pI (isoelectric point), which in the case of hGH, is 5.3. In one particularly preferred embodiment of the invention, a suspension comprising trileucine in solution and the 4-α helical protein, hGH, in suspension at pH 5.3, is spray dried.

The aqueous formulation may optionally contain additional water-miscible solvents, such as acetone, alcohols and the like. Representative alcohols are lower alcohols such as methanol, ethanol, propanol, isopropanol, and the like. Such mixed solvent systems will typically contain from about 0–80% of the water miscible solvent, more preferably from about 20–40%, and most preferably from about 10–30% of the water miscible solvent. The pre-spray dried solutions will generally contain solids dissolved at a concentration from 0.01% (weight/volume) to about 20% (weight/volume), usually from 0.05% to 10% (weight/volume, e.g., mg/ml), and preferably from about 0.1 to 2% (weight/volume, i.e., 1–20 mg/ml). Specifically, the pre-spray dried formulation will typically possess one of the following solids concentrations: 0.1 mg/ml or greater, 0.5 mg/ml or greater, 1 mg/ml or greater, 1.5 mg/ml or greater, 2 mg/ml or greater, 3 mg/ml or greater, 4 mg/ml or greater, or 5 mg/ml or greater. Preferred are solids concentrations from about 10–15 mg/ml. In one embodiment of the invention, the protein is spray dried at a solids concentration of 0.1 mg/mil, which is effective to provide a spray dried solid in which the native protein conformation is retained. Preferred embodiments of the invention will thus employ optimal solids concentrations during spray drying, optionally in concert with one or more stabilizers to provide respirable powders having minimized protein aggregation and superior aerosol properties.

Also, while working within solids concentrations which maintain alpha helicity of the protein (as described above), it is preferable to spray dry the protein at the higher ends (i.e., higher solids content) of the preferred concentration ranges, since higher protein concentrations correspond to high amounts of protein in a droplet, which will decrease the relative percentage of protein that can be denatured on the droplet surface due to contact with an air-water interface. Thus, if one assumes that only a certain number of protein molecules fit on a droplet surface, and that only those molecules are susceptible (or at least are most susceptible) to denaturation, then the remaining non-surface positioned protein molecules represent "protected payload".

The solutions are then spray dried in a conventional spray drier, such as those available from commercial suppliers such as Niro A/S (Denmark), Buchi (Switzerland) and the like, resulting in a dispersible, dry powder. Optimal conditions for spray drying the solutions will vary depending upon the formulation components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause decomposition of the active agent in the sprayed material. Such temperatures are typically determined experimentally, although generally, the inlet temperature will range from about 50° C. to about 200° C., while the outlet temperature will range from about 30° C. to about 150° C. Preferred parameters include atomization pressures ranging from about 20–150 psi, and preferably from about 30–40 to 100 psi. Typically the atomization pressure employed will be one of the following (psi): 20, 30, 40, 50, 60, 70, 80, 90, 100, 110, 120 or above. Spray dried powders are physically distinct from powders prepared by other evaporative drying methods, and typically exhibit morphologies and thermal histories (including glass transition temperatures, glass transition widths, and enthalpic relaxation profiles) that differ from those of powders prepared by other drying methods such as lyophilization.

Once formed, the 4-α helix bundle protein dry powder compositions are preferably maintained under dry (i.e., relatively low humidity) conditions during manufacture, processing, and storage. Irrespective of the particular drying parameters employed, the spray drying process will preferably result in inhaleable, non-protein aggregated, highly dispersible particles comprising an active 4-α helical bundle protein, preferably human growth hormone.

V. Features of Dry Powder Formulations

Powders of the invention are further characterized by several features, most notably, (i) consistently high dispersibilities, which are maintained, even upon storage (ii) small aerodynamic particles sizes (MMADs), (iii) improved fine particle dose values, i.e., powders having a higher percentage of particles sized less than 3.3 microns MMAD, all of which contribute to the improved ability of the powder to penetrate to the tissues of the lower respiratory tract (i.e., the alveoli) for systemic treatment by a protein such as hGH. These physical characteristics of the spray dried powders of the invention, to be described more fully below, are important in maximizing the efficiency of aerosolized delivery of such powders to the deep lung.

Dry powders of the invention are composed of aerosolizable particles effective to penetrate into the lungs. The particles of the invention have a mass median diameter (MMD) of less than about 20 μm, preferably less than about 10 μm, more preferably less than about 7.5 μm, and most preferably less than about 4 μm, and even more preferably less than about 3.5 μm, and usually are in the range of 0.1 μm to 5 μm in diameter. Preferred powders are composed of particles having an MMD from about 0.2 to 4.0 μm. In some cases, the powder will also contain non-respirable carrier particles such as lactose, where the non-respirable particles are typically greater than about 40 microns in size.

The powders of the invention are further characterized by an aerosol particle size distribution less than about 10 μm mass median aerodynamic diameter (MMAD), preferably having MMADs less than about 5 μm, more preferably less than 4.0 μm, even more preferably less than 3.5 μm, and most preferably less than 3 μm. The mass median aerodynamic diameters of the powders will characteristically range from about 0.1–10 μm, preferably from about 0.2–5.0 μm MMAD, more preferably from about 1.0–4.0 μm MMAD, and even more preferably from about 1.5 to 3.0 μm. Illustrative MMAD values for exemplary spray dried hGH powders are provided in the Examples. Several of these examples demonstrate an improvement in aerosol particle size distribution achieved by a combination of optimized spray drying conditions and choice and concentration of stabilizer.

The powders of the invention may further be characterized by their densities. The powder will generally possess a bulk density from about 0.1 to 10 g/cubic centimeter, preferably from about 0.1–2 g/cubic centimeter, and more preferably from about 0.15–1.5 g/cubic centimeter.

The powders will generally have a moisture content below about 20% by weight, usually below about 10% by weight, and preferably below about 6% by weight. More preferably, the spray dried powders will typically possess a residual moisture content below about 3%, more preferably below about 2%, and most preferably between about 0.5 and 2% by weight. Such low moisture-containing solids tend to exhibit a greater stability upon packaging and storage. Generally, the powders of the invention are hygroscopic, i.e., they demonstrate a tendency to absorb moisture from the atmosphere if not stored in sealed containers such as blister packages.

One of the most striking features of the compositions of the invention is their high dispersibilities, as indicated by the ED value. The spray drying methods and stabilizers described herein are effective to provide formulations having significantly improved dispersibilities over their non-optimized counterparts. Generally, the emitted dose (ED) of these powders is greater than 30%, and usually greater than 40%. More preferably, the ED of the powders of the invention is greater than 50%, and is often greater than 55%. In fact, in looking at the Examples, the spray dried powders of the invention typically possess optimized ED values exceeding 65%, and often ranging from about 70–90% or greater.

An additional measure for characterizing the overall aerosol performance of a dry powder is the fine particle fraction (FPF), which describes the percentage of powder having an aerodynamic diameter less than 3.3 microns. The powders of the invention are particularly well suited for pulmonary delivery, and possess FPF values ranging from about 30%–64% or more. Preferred powders contain at least about 30 percent of aerosol particle sizes below 3.3 μm to about 0.5 μm and are thus extremely effective when delivered in aerosolized form, in reaching the regions of the lung, including the alveoli.

The compositions described herein also possess good stability with respect to both chemical stability and physical stability, i.e., aerosol performance over time. Generally, with respect to chemical stability, the 4-α helix bundle protein contained in the formulation will degrade by no more than about 10% upon spray drying. That is to say, the powder will possess at least about 90% intact active protein, preferably at least about 95% intact active agent, and even more preferably will contain at least about 97% or greater intact active agent. Preferably, the spray drying process will result in powders having less than about 10% total protein aggregates, preferably less than about 7% total aggregates, and most preferably, less than 5–6% total aggregates. More specifically, the spray dried powder will typically possess less than about 10% insoluble aggregates, preferably less than about 7% insoluble aggregates, and more preferably will contain less than about 5% insoluble aggregates. In considering soluble aggregates, the spray dried powder will typically contain less than 7% soluble aggregates, preferably less than 6% soluble aggregates, more preferably less than 5% soluble aggregates, and most preferably less than 4%, 3%, 2% or 1% soluble aggregates. The total amount of monomer in the spray dried particles is typically greater than 90%, and is more preferably greater than one of the following: 91%, 92%, 93%, 94%, or 95%. Moreover, the compositions of the invention further demonstrate good stability upon storage, as characterized by a total protein aggregate content of less than about 10% after storage for one month at 40° C. and ambient relative humidity. That is to say, the total aggregate content of many of the exemplary growth hormone compositions of the invention remained substantially unchanged upon storage for one month at 40° C., thus illustrating the attainment of an optimized balance of both chemical and physical stability upon both spray drying and storage of the inhaleable growth hormone compositions of the invention.

With respect to aerosol performance, compositions of the invention are generally characterized by a drop in emitted dose of no more than about 20%, preferably no more than about 15%, and more preferably by no more than about 10%, when stored under ambient conditions for a period of three months.

The improvement in aerosol properties noted for the compositions herein, along with minimized protein aggregation, can result in several related advantages, such as: (i) reducing costly drug loses to the inhalation device, since more powder is aerosolized and is therefore available for inhalation by a subject; (ii) reducing the amount of dry powder required per unit dose, due to the high efficiency of aerosolization of powder; and (iii) reducing the number of inhalations per day by increasing the amount of aerosolized drug reaching the lungs of a subject.

VI. Administration of the Composition

The formulations described herein may be delivered using any suitable dry powder inhaler (DPI), i.e., an inhaler device that utilizes the patient's inhaled breath as a vehicle to transport the dry powder drug to the lungs. Preferred are Inhale Therapeutic Systems' dry powder inhalation devices as described in Patton, J. S., et al., U.S. Pat. No. 5,458,135 (1995) Smith, A. E., et al., U.S. Pat. No. 5,740,794 (1998); and in Smith, A. E., et. al., U.S. Pat. No. 5,785,049 (1998), Schuler, C., et al., International Patent Publication No. WO 01/00263, herein incorporated by reference.

When administered using a device of this type, the powder is contained in a receptacle having a puncturable lid or other access surface, preferably a blister package or cartridge, where the receptable may contain a single dosage unit or multiple dosage units. Convenient methods for filling large numbers of cavities (i.e., unit dose packages) with metered doses of dry powder medicament are described, e.g., in Parks, D. J., et al., WO 97/41031 (1997) incorporated herein by reference.

Also suitable for delivering the powders described herein are dry powder inhalers of the type described, for example, in Cocozza, S., et al., U.S. Pat. No. 3,906,950 (1974), and in Cocozza, S., et al., U.S. Pat. No. 4,013,075 (1997), incorporated herein by reference, wherein a premeasured dose of dry powder for delivery to a subject is contained within a hard gelatin capsule.

Other dry powder dispersion devices for pulmonarily administering dry powders include those described, for example, in Newell, R. E., et al, European Patent No. EP 129985 (1988); in Hodson, P. D., et al, European Patent No. EP 472598 (1996); in Cocozza, S., et al., European Patent No. EP 467172 (1994), and in Lloyd, L. J. et al., U.S. Pat. No. 5,522,385 (1996), incorporated herein by reference. Also suitable for delivering the dry powders of the invention are inhalation devices such as the Astra-Draco "TURBUHALER". This type of device is described in detail in Virtanen, R., U.S. Pat. No. 4,668,281 (1987); in Wetterlin, K., et al U.S. Pat. No. 4,667,668 (1987); and in Wetterlin, K., et al. U.S. Pat. No. 4,805,811 (1989), all of which are incorporated herein by reference. Other suitable devices include dry powder inhalers such as the Rotahaler® (Glaxo), Discus® (Glaxo), Spiros™ inhaler (Dura Pharmaceuticals), and the Spinhaler® (Fisons). Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in Mulhauser, P., et al, U.S. Pat. No. 5,388,572 (1997), incorporated herein by reference.

Dry powders may also be delivered using a pressurized, metered dose inhaler (MDI), e.g., the Ventolin® metered dose inhaler, containing a solution or suspension of drug in a pharmaceutically inert liquid propellant, e.g., a chlorofluorocarbon or fluorocarbon, as described in Laube, et al., U.S. Pat. No. 5,320,094 (1994), and in Rubsamen, R. M., et al, U.S. Pat. No. 5,672,581 (1994), both incorporated herein by reference. Alternatively, the powders described herein may be dissolved or suspended in a solvent, e.g., water, ethanol, or saline, and administered by nebulization. Nebulizers for delivering an aerosolized solution include the AERx™ (Aradigm), the Ultravent® (Mallinkrodt), and the Acorn II (Marquest Medical Products).

Prior to use, dry powders are generally stored under ambient conditions, and preferably are stored at temperatures at or below about 25° C., and relative humidities (RH) ranging from about 30 to 60%. More preferred relative humidity conditions, e.g., less than about 30%, may be achieved by the incorporation of a dessicating agent in the secondary packaging of the dosage form.

VII. Utility

The compositions of the invention are useful, when administered pulmonarily in a therapeutically effective amount to a mammalian subject, for treating or preventing any condition responsive to the administration of a 4-α helix bundle protein as described in section II.A above.

In particular, the exemplary 4-α helix bundle protein, hGH, when administered in therapeutically effective amounts, is useful in the treatment of conditions such as pediatric growth hormone deficiency, adult growth hormone deficiency, chronic renal insufficiency, and Turner syndrome.

The following examples are illustrative of the present invention, and are not to be construed as limiting the scope of the invention. Variations and equivalents of this example will be apparent to those of skill in the art in light of the present disclosure, the drawings and the claims herein.

All articles, books, patents and other publications referenced herein are hereby incorporated by reference in their entirety.

EXAMPLES

Materials and Methods

A. Materials.

- Des-phe human growth hormone (des-phe hGH), BresaGen Limited, Adelaide, South Australia
- Native human growth hormone, BresaGen Limited, Adelaide, South Australia
- Methionyl-human growth hormone (met hGH), BresaGen Limited, Adelaide, South Australia
- L-Leucine (Aldrich, St. Louis, Mo.)
- Ethanol, 200 proof (USP/NF, Spectrum Chemical Mfg. Corp., New Brunswick, N.J.)
- Methanol (HPLC grade, EM Industries, Gibbstown, N.J.)
- Trileucine (Bachem California Inc, USA Torrance, Calif.).
- Sodium phosphate, dibasic, 7-hydrate crystal: J. T. Baker, Lot No.: M30150.
- Sodium phosphate, monobasic, monohydrate: J. T. Baker, Lot No.: N50156.
- Sucrose: T. J. Baker, Lot No.: N21593.
- Raffinose, pentahydrate: Pfanstiehl, Lot No.: 25320A.
- Trehalose, dihydrate: Spectrum, Lot No.: OF0359.
- Ile: Sigma, 98%, Lot No. 28H00462.
- Val: Aldrich, 99%, Lot No. 08311AU.
- Phe: Aldrich, 99%, Lot No. 13022TS.
- Trp: Aldrich, 99%, Lot No. 12729HS.

B. Methods.

Particle Size Measurements (Horiba)

Mass median diameters (MMD) of the powders were measured using a Horiba CAPA-700 particle size analyzer (Horiba Instruments inc., Irvine, Calif.). Measurements were based upon centrifugal sedimentation of dispersed particles in suspending medium. Mass median diameter, which is based on the particle's Stokes' diameter, was calculated using the particle density and the density and viscosity of the suspending medium.

The density of the powder was set as 1.5 g/cm$^3$ for all powders. (This nominal value was used for all powders analyzed and is within a range that is typical for spray dried powders). Particle size measurements were conducted with about 5–10 mg powder suspended in 5 ml Sedisperse A-11 (Micromeritics, Norcross, Ga.) and dispersed by sonication for 10 minutes. The range over which particle size data was gathered was set to 0.4 to 10.0 μm.

Particle Size (VMD):

Particle size distributions were measured using a SYMPATEC HELOS particle size analyzer operated at a shear force of 2 bar. A focal length corresponding to R2 was used in combination with a type 1DR detector. Volume mean diameter (VMD) was obtained from the distributions.

Chemical Stability.

Protein purity/extent of protein degradation was determined by reverse phase HPLC (RP-IPLC).

Moisture Content.

Residual moisture content of the powders was determined by the Karl Fischer titrimetric technique using a Mitsubishi moisture meter Model # CA-06. Moisture content may also be determined by thermal gravimetric analysis (TGA).

Soluble Aggregate Determination.

Soluble aggregates were measured by size exclusion high pressure liquid chromatography or SEC using a Waters HPLC system equipped with a solvent delivery system, a photo diode array detector, a temperature controlled autosampler, and data management system.

Insoluble Aggregate Determination.

Insoluble aggregates were determined by ultraviolet spectroscopy (UV) using a Shimadzu UV-2101 PC dual spectrophotometer. Samples are scanned over a range of 360 to 240 nm. Insoluble aggregates were determined quantitatively by measuring the turbidity of the solution (Eckhardt, B. M. et al., *Pharm Res.,* 8(11), 1360–1364 (1991).

Aerodynamic Particle Size Measurements

Andersen Cascade Impactor.

An Andersen cascade impactor (a sieve-like apparatus with a series of stages that capture particles on plates by inertial impaction according to their size) was used to determine the MMAD and particle size distribution of aerosolized powder formulations in an air stream. The plates were weighed before and after testing and the mass of powder deposited on the plate of each stage was determined. Unless otherwise indicated, studies were undertaken using a traditional Andersen cascade impactor having eight stages (from top to bottom stages 0 to 7) with cut-off sizes ranging from 9.0 to 0.4 μm, and a final filter stage that traps particles <0.4 μm when operated at a flow rate of 28.3 L/min. The device test set-up was similar to the ED test, except that the cascade impactor and a USP (United States Pharmacopia) throat (USP 23, chapter <601>) were attached to the device mouthpiece rather than to a filter. Multiple dispersions were typically conducted for each cascade impaction run to achieve gravimetrically accurate data.

Andersen Short Stack (SS) Method.

In the SS method, the order in which the stages were placed were altered from the conventional Andersen cascade impactor set-up as described above. From the top, stage 0 was utilized for inlet cone attachment to connect the throat. Stage 3 was positioned next, beneath stage 0, followed by the filter stage (stage F). The powder-containing airstream passes only through stages 0 and 3; air (but not powder) flows through the other stages, which are placed under stage F to hold the remainder of the assembly in place. A pre-weighed filter was placed on stage F and captured particles <3.3 μm. A second filter was placed on an inverted plate under stage 3, and captured particles >3.3 μm. For the studies described herein, one BP (blister pack) containing 2 mg of powder composition was dispersed in an aerosol delivery device and a vacuum was pulled at 28.3 L/min as per USP methodology. This process was then repeated two times for a target mass of 6 mg per run. The filters were then removed and weighed to determine the amount of powder deposited.

Example 1

Neat hGH Formulation for Pulmonary Delivery

Native full-length hGH (n-hGH, BresaGen native full-length, catalog number hST-3, lot H057) was spray-dried neat (i.e., absent excipients/stabilizers). The physical and chemical stability and aerosol properties of the resulting powder were evaluated immediately after spray drying and after storage for 1 month at three different temperatures.

Solution Preparation.

Prior to spray drying, the protein was diafiltered using an Amicon (Millipore) Ultrafiltration cell with a YM-10 membrane to remove the mannitol and glycine contained in the commercial formulation. A solution containining hGH (725 mg) and 5 mM sodium phosphate at pH 7.8 was prepared. The liquid formulation contained 10 mg solids per ml (i.e., 1% total solids content). The buffer represented 6.9% of total solids, and [hGH] was 93.1% of total solids, or 9.31 mg/ml.

Spray Drying.

The neat formulation was spray dried using a Buchi 190 mini spray dryer (Buchi Labortechnik AG, Meierseggstrasse, Switzerland) with a modified cyclone (Platz, R., et al., Inhale Therapeutic Systems' International Patent Publication No. WO 97/41833, Nov. 13, 1997), atomizer nozzle and powder collection vessel. The collection efficiency was above 70%; typical collection efficiencies ranged from about 75–95%.

Powder Packaging and Characterization.

The resulting powder was hand filled into 5 mg unit dosage forms (blister packs, BPs) in a glove box with a relative humidity less than 5%. The BPs were pouched with desiccant and stored at three different temperatures, 4° C., 25° C., and 40° C., for 1 month. The physical (aerosol performance) and chemical properties of the powder were then assessed using the methodologies described generally above.

TABLE 1

Characterization of Spray-Dried Neat hGH

| | t = 0 | t = 1 month, 4° C. | t = 1 month, 25° C. | t = 1 month, 40° C. |
|---|---|---|---|---|
| ED, % | 72 | 76 | 74 | 73 |
| MMAD, μ | 3.5 | 3.8 | 3.4 | 3.6 |
| FPF | 45% | 40% | 47% | 41% |
| Moisture Content | 1.9% | 2.0% | 2.0% | 2.2% |
| Insol. Aggreg. (UV) | 1.4% | 1.8% | 2.0% | 1.8% |
| Sol. Aggreg. (SEC) | 5% | 2% | 4% | 6% |
| Protein Purity | 97.0% | 96.8% | 96.0% | 94.7% |

The above data indicates that certain spray drying conditions (solids content, atomization pressure, pH, and the like) can by utilized to prepare hGH dry powders having high dispersibilities (EDs greater than 70%), good aerodynamic size range (MMADs averaging about 3.5 microns), a low extent of protein degradation (less than about 5%), and combined soluble and insoluble aggregates of less than 8% when stored at 40° C., less than about 6% when stored under ambient conditions, and less than about 4% when stored at low temperatures.

Example 2

Spray Drying Neat hGH Under a Variety of Process Conditions

Aqueous solutions of human growth hormone absent additional excipients/stabilizers were prepared and spray dried as described above under a variety of different process conditions to examine the effect(s) upon the characteristics of the resulting powders.

A summary of relevant process parameters and properties of the resulting dried powders is provided in Table 2 below. IA=insoluble aggregates; SA=soluble aggregates.

TABLE 2

Spray Dried Neat hGH

| Expt No | Solids (%) | Atom. (psi) | MMAD (microns) | ED (%) | IA (%) | SA (%) | hGH (type) |
|---|---|---|---|---|---|---|---|
| S3-01 | 1 | 40 | 3.5 | 72 | 0.7 | 5.1 | Native |
| S4-03 | 1 | 80 | 3.3 | 76 | 0.5 | 2.5 | Met |
| S5-04 | 1.1 | 60 | 3.8 | 76 | 1.1 | 2.6 | Met |
| S6-01 | 0.5 | 60 | 3.4 | 83 | 0.3 | 5.3 | D-Phe |
| S6-02 | 1 | 60 | 3.8 | 77 | 0.1 | 3.9 | D-Phe |
| S6-03 | 1 | 40 | 4.1 | 72 | 0.5 | 4.1 | D-Phe |
| S6-04 | 2 | 40 | 4.3 | 72 | 0.6 | 3.1 | D-Phe |
| S7-07 | 1 | 80 | 3.3 | 79 | 0.1 | 3.3 | Met |

The above data further supports the utility of the herein described preferred process parameters in preparing 4 α-helical bundle protein powders that exhibit mimimal protein aggregation upon spray drying and have superior aerosol properties (EDs greater than 70% and MMADs averaging about 3 microns).

Example 3

Respirable Spray Dried hGH Formulations Comprising Trileucine

The objective of this study was to determine the effect of trileucine on the aerosol properties as well as the 1 -month stability of spray-dried Met-hGH.

A. Formulation

Five different formulation solutions were prepared as follows. Methionyl-human growth hormone was mixed at a concentration of 7 mg/mL (70% w/w) with trileucine (L3) at concentrations of 1.5 and 3 mg/mL to provide powders comprising 15% and 30% by weight trileucine, respectively. These solutions were adjusted to pH 3.6 or 7.8. Similarly, an aqueous solution of methionyl-human growth hormone (10 mg/ml) and sodium phosphate (5 mM) at pH 7.8 was prepared. All formulations were prepared at a total solids content of 1%.

B. Spray Drying The above-described hGH solutions were spray dried using a Buchi 190 laboratory scale spray drier as described in Examples 1 and 2 above; the atomization pressure employed was 80 psi.

C. Characterization

Aerosol properties and chemical stability of the spray-dried Met-hGH powders are provided below:

TABLE 3

Spray Dried hGH-Trileucine (L3) Powders

| | 15% L3 pH 3.6 | 30% L3 pH 3.6 | 0% L3 pH 7.8 | 15% L3 pH 7.8 | 30% L3 pH 7.8 |
|---|---|---|---|---|---|
| ED | 92% | 88% | 76% | 75% | 73% |
| MMAD | 2.6 | 3.1 | 3.3 | 3.3 | 3.1 |
| VMOD | 2.3 | 2.5 | 1.9 | 1.7 | 2.0 |
| FPF | 64% | 54% | 49% | 51% | 55% |
| Moisture Content | 0.9% | 0.9% | 1.0% | 1.3% | 1.3% |
| Insol. Aggreg. | | | | | |
| Sol. Aggreg. | 1.0% | 1.8% | 2.5% | 0.4% | 0.5% |
| Protein Purity | 95.3% | 95.8% | 95.2% | 95.9% | 95.7% |

The above data indicates that trileucine is an effective stabilizer when employed during spray-drying a representative 4 α-helical bundle protein such as hGH. Moreoever, the low pH conditions utilized during spray drying appear to enhance the dispersibility, and in particular when used in combination with trileucine, provides cooperative stabilization of the growth hormone molecule to provide powders which exhibit a minimal degree of protein degradation, and possess both superior EDs (averaging about 90%) and small aerodynamic diameters (ranging from about 2.6–3.1 microns).

Example 4

Respirable Spray Dried hGH Formulations Comprising Sugars

The objective of this study was to explore the use of sugars as stabilizers along with optimized process parameters in spray-drying formulations of hGH to achieve powders with desirable aerosol properties and good hGH stability profiles.

Among the numerous sugars, non-reducing sugars, sugars that can form an amorphous phase when combined with protein in a dried solid, and sugars with high Tgs (e.g., having glass transition temperatures greater than 30 C, preferably greater than 40 C, more preferably greater than 50° C., even more preferably greater than 60° C., and most preferably greater than 70° C. ) are preferred. In keeping with these preferences, sucrose (Tg=74° C.), raffinose (Tg=102° C.) and trehalose (Tg=115° C.) were employed in this study (Tg data from A. Saleki-Gerdt, Zografi, G., *Pharm Res.,* 11(8), 1166–1172 (1994)).

A. Formulation Preparation.

A 5 mM sodium phosphate buffer solution at pH 7.8 was prepared. Each met-hGH lyophile vial was reconstituted with 5 ml of HPLC water. A total of 18 vials was used. The hGH solution was diafiltered to remove excipients prior to reformulation. The diafiltration set up used was an Amicon (Millipore) Ultrafiltration cell with an YM 10,000 filter. The protein solution was diafiltrated using the 5 mM sodium phosphate buffer pH 7.8 and a gas pressure of 37 psig at 4–5° C. for 11 hours. After the diafiltration step, the protein concentration was checked by UV spectroscopy at 277 nm and the concentration was adjusted to 12.1 mg/mil with the 5 mM sodium phosphate buffer at pH 7.8.

Stock sugar solutions were prepared at concentrations of 22.8, 22.7 and 22.7 mg/mL for sucrose, raffinose and trehalose, respectively. These solutions were prepared in 5 mM sodium phosphate at pH 7.8. Four formulations were prepared in centrifuge tubes labeled with S5-01 (sucrose), S5-02 (trehalose), S5-03 (raffinose) and S5-04 (buffer only), respectively. S5-01: 40 ml of 12.1 mg/ml hGH was dispensed into a bottle, and 10 ml of sucrose stock was added. The pH was adjusted to 7.8. S5-02: 40 ml of 12.1 mg/ml hGH was dispensed into a bottle, and 10 ml of raffinose stock was added. The pH was adjusted to 7.8. S5-03: 34 ml of 12.1 mg/ml hGH was dispensed into a bottle, to which was added 8.5 ml of trehalose stock solution. The pH was adjusted to 7.8. S5-04: 40 ml of 12.1 mg/ml hGH was dispensed into a bottle, to which was added 10 ml of 5 MM sodium phosphate buffer at pH 7.8. The pH was adjusted to 7.8. A formulations summary is provided in Table 4 below.

TABLE 4

| Formulation Summary | | | | | | | | | |
|---|---|---|---|---|---|---|---|---|---|
| | | hGH | Sugar | | Buffer | % of Total Solid | | | Total solid |
| Formulation | pH | (mg/mL) | | (mg/mL) | (mM) | hGH | Sugar | Buffer | (%) |
| S5-01 | 7.8 | 9.7 | Sucrose | 4.55 | 5 | 64.9 | 30.5 | 4.6 | 1.5 |
| S5-02 | 7.8 | 9.7 | Raffinose | 4.55 | 5 | 64.9 | 30.5 | 4.6 | 1.5 |
| S5-03 | 7.8 | 9.7 | Trehalose | 4.55 | 5 | 64.9 | 30.4 | 4.6 | 1.5 |
| S5-04 | 7.8 | 9.7 | Neat | 0 | 5 | 93.4 | 0.0 | 6.6 | 1.0 |

B. Spray Drying:

The formulation solutions described above were spray-dried using a Buchi 190 mini spray dryer as described in the above Examples. Spray drying was carried out at an atomization pressure of 60 psi and an outlet air temperature of 60° C. Powders were collected with yields ranging from about 60–85%.

C. Stability.

The powders were transferred into a glove box with a relative humidity less than 5% and transferred to unit dosage forms (5.0 mg of powder in each blister pack) which were heat sealed with lidstock. Blisters from each formulation were placed into a 40° C. temperature station. The blisters were sealed in an aluminum bag with desiccants. Samples were removed from the temperature station at the one-month time point.

The results of aerosol performance, protein aggregate, protein purity and residiual moisture analyses are presented in tabular form below.

TABLE 5

| Emitted Dose at initial and one month time points | | | | | | | | |
|---|---|---|---|---|---|---|---|---|
| | | | Initial time point | | | One-month time point | | |
| Formulation | Description | pH | ED % | SD | RSD % | ED % | SD | RSD % |
| S5-01 | 30% sucrose | 7.8 | 75.0 | ±2.8 | 3.7 | 75.9 | ±3.8 | 5.1 |
| S5-02 | 30% raffinose | 7.8 | 77.4 | ±3.0 | 3.8 | 76.5 | ±3.1 | 4.0 |
| S5-03 | 30% trehalose | 7.8 | 80.1 | ±2.2 | 2.7 | 76.8 | ±2.4 | 3.1 |
| S5-04 | neat | 7.8 | 82.9 | ±3.0 | 3.6 | 78.5 | ±4.3 | 5.4 |

The data indicate that ED for all formulations tested was above 75%. The hGH powders formulated with three sugars (30%) did not provide higher ED when compared to the neat formulation. Upon storage of the pouched powders at 40° C. for one month, the ED didn't change significantly although a slight decrease in ED for trehalose and neat formulations was observed.

TABLE 6

| MMAD, FPF at initial and one month time points | | | | | | | | |
|---|---|---|---|---|---|---|---|---|
| | | | | | | One-month time point | | |
| Formulation | Description | PH | MMAD (μm) | FPF (%) | VMD (μm) | MMAD (μm) | FPF (%) | VMD (μm) |
| S5-01 | 30% sucrose | 7.8 | 3.9 | 36 | 2.4 | 3.4 | 48 | 2.2 |
| S5-02 | 30% raffinose | 7.8 | 3.9 | 37 | 2.5 | 3.9 | 37 | 2.3 |
| S5-03 | 30% trehalose | 7.8 | 3.8 | 38 | 2.5 | 4.0 | 35 | 2.3 |
| S5-04 | neat | 7.8 | 3.8 | 39 | 2.3 | 3.9 | 37 | 2.2 |

Powders from the four formulations had similar MMAD (3.8–3.9 μm) values. It was observed that the values of MMAD remained in the same range after one-month storage at 40° C. with the exception of the sucrose formulation (3.4 μm). A decrease in MMAD for the sucrose formulation may have resulted from an unexpected experimental error since the CIE from the measurement had a value of 115% (over 100%). The particle size distributions for the other formulations were very consistent between the initial and one-month time points.

TABLE 7

| Moisture content | | | | |
|---|---|---|---|---|
| Formulation | Desciption | pH | Inintial time point (%) | One-month time point (%) |
| S5-01 | 30% sucrose | 7.8 | 1.1 | 1.0 |
| S5-02 | 30% raffinose | 7.8 | 1.6 | 1.4 |
| S5-03 | 30% trehalose | 7.8 | 1.4 | 1.3 |
| S5-04 | neat | 7.8 | 1.2 | 1.4 |

The moisture was in a range from 1 to 1.6%. As expected, the moisture level did not increase after one month storage at 40° C. with desiccants.

TABLE 8

| Characterization of Chemical Degradation by RP-HPLC | | | | | | | | |
|---|---|---|---|---|---|---|---|---|
| Time point | | | Average of 3 injections (%) | | | | | |
| (Month) | Formulation | Description | hGH | SD | % RSD | EE | SD | % RSD |
| 0 | H051RP | Starting met-hGH | 94.50 | ±0.34 | 0.36 | 5.49 | ±0.34 | 6.10 |
| 0 | After diafiltratn. | pre-formulatn | 94.62 | ±0.32 | 0.34 | 5.38 | ±0.32 | 5.96 |
| 0 | S5-01 | 30% sucrose | 94.29 | ±0.44 | 0.47 | 5.71 | ±0.44 | 7.74 |
| 0 | S5-02 | 30% raffinose | 94.50 | ±0.20 | 0.21 | 5.50 | ±0.20 | 3.58 |
| 0 | S5-03 | 30% trehalose | 94.41 | ±0.67 | 0.71 | 5.59 | ±0.67 | 12.05 |
| 0 | S5-04 | neat | 94.31 | ±0.40 | 0.43 | 5.69 | ±0.40 | 7.06 |
| 1 | H051RP | Fresh reconstituted | 96.07 | ±0.21 | 0.22 | 3.93 | ±0.21 | 5.29 |
| 1 | S5-01 | 30% sucrose | 95.17 | ±0.35 | 0.37 | 4.83 | ±0.35 | 7.25 |
| 1 | S5-02 | 30% raffinose | 94.30 | ±0.36 | 0.38 | 5.70 | ±0.36 | 6.32 |
| 1 | S5-03 | 30% trehalose | 94.87 | ±0.26 | 0.27 | 5.13 | ±0.26 | 5.07 |
| 1 | S5-04 | neat | 94.15 | ±0.41 | 0.44 | 5.85 | ±0.41 | 7.06 |

The data reveal that the percentages of hGH and early-eluted peaks (EE) remained at similar levels after one month storage at 40° C. for all formulations tested. No significant differences in the amounts of hGH and EE between the formulations prepared were observed in the RP-HPLC analysis.

TABLE 9

| Characterization of soluble aggregates (SA) by SE-HPLC | | | | | | | | |
|---|---|---|---|---|---|---|---|---|
| Time point | | | Average of 3 injections (%) | | | | | |
| (Month) | Formulation | Description | hGH | SD | % RSD | SA | SD | % RSD |
| 0 | H051RP | Starting met-hGH | 99.69 | ±0.01 | 0.01 | 0.31 | ±0.01 | 3.69 |
| 0 | After diafiltratn. | pre-formulatn | 99.67 | ±0.05 | 0.05 | 0.33 | ±0.05 | 14.18 |
| 0 | S5-01 | 30% sucrose | 98.04 | ±0.27 | 0.27 | 1.96 | ±0.27 | 13.70 |
| 0 | S5-02 | 30% raffinose | 97.74 | ±0.18 | 0.18 | 2.26 | ±0.18 | 7.78 |
| 0 | S5-03 | 30% trehalose | 97.66 | ±0.10 | 0.10 | 2.34 | ±0.10 | 4.08 |
| 0 | S5-04 | neat | 97.47 | ±0.07 | 0.07 | 2.53 | ±0.07 | 2.59 |
| 1 | H051RP | Fresh reconstituted | 99.91 | ±0.02 | 0.02 | 0.09 | ±0.02 | 16.37 |
| 1 | S5-01 | 30% sucrose | 97.39 | ±0.17 | 0.17 | 2.61 | ±0.17 | 6.37 |
| 1 | S5-02 | 30% raffinose | 96.65 | ±0.03 | 0.03 | 3.35 | ±0.03 | 0.96 |
| 1 | S5-03 | 30% trehalose | 96.78 | ±0.04 | 0.05 | 3.22 | ±0.04 | 1.35 |
| 1 | S5-04 | neat | 95.32 | ±0.06 | 0.07 | 4.68 | ±0.06 | 1.37 |

The soluble aggregates (SA) increased slightly after spray-drying all of the formulations (to about 2%). After one month's storage at 40° C. with desiccants, the soluble aggregates increased slightly. The soluble aggregates for the neat formulation increased to 4.7%. This may suggest that sugars such as these stabilize the hGH protein against aggregation. Among the three sugar formulations, the sucrose formulation exhibited the lowest value of soluble aggregate percentages at both the initial and one-month time points.

TABLE 10

| Characterization of insoluble aggregates by UV spectroscopy | | | | | |
|---|---|---|---|---|---|
| Time point | | | Average of 3 injections (%) | | |
| (Month) | Formulation | Description | hGH | SD | % RSD |
| 0 | H051RP | Starting met-hGH | 1.9 | | |
| 0 | After diafiltratn. | pre-formulatn | 0.2 | | |
| 0 | S5-01 | 30% sucrose | 0.0 | | |
| 0 | S5-02 | 30% raffinose | 2.9 | | |

TABLE 10-continued

| Characterization of insoluble aggregates by UV spectroscopy | | | | | |
|---|---|---|---|---|---|
| Time point | | | Average of 3 injections (%) | | |
| (Month) | Formulation | Description | hGH | SD | % RSD |
| 0 | S5-03 | 30% trehalose | 1.6 | | |
| 0 | S5-04 | neat | 2.0 | | |
| 1 | S5-01 | 30% sucrose | 1.7 | 0.2 | 13.8 |
| 1 | S5-02 | 30% raffinose | 1.9 | 0.1 | 3.7 |
| 1 | S5-03 | 30% trehalose | 2.4 | 0.5 | 21.5 |
| 1 | S5-04 | neat | 1.3 | 0.2 | 11.9 |

The insoluble aggregates were below 3% for all formulations tested. No increase in insoluble aggregates was observed after one month storage at 40° C. The SD and %RSD reported in the Table 9 for one month time point were obtained from the triple scans of same samples. It reflects variations of UV measurement from same samples, but not in variations from sample to sample.

The percentage of total monomer (TM) was also calculated as described by B. M. Eckhardt, J. Q. Oeswein, and T. A. Bewley, *Pharm. Res.,* 8(11): 1360–1364 (1991).

TABLE 11

Calculation of percent total monomer

| Time point (Month) | Formulation | Description | (%) IA | (%) SA | (%) TM |
|---|---|---|---|---|---|
| 0 | H051RP | Starting met-hGH | 1.9 | 0.31 | 97.5 |
| 0 | After diafiltratn. | pre-formulatn | 0.2 | 0.33 | 99.6 |
| 0 | S5-01 | 30% sucrose | 0.0 | 1.96 | 99.7 |
| 0 | S5-02 | 30% raffinose | 4.6 | 2.26 | 93.2 |
| 0 | S5-03 | 30% trehalose | 1.6 | 2.34 | 96.1 |
| 0 | S5-04 | neat | 2.0 | 2.53 | 95.5 |
| 1 | S5-01 | 30% sucrose | 1.7 | 2.61 | 95.7 |
| 1 | S5-02 | 30% raffinose | 1.9 | 3.35 | 94.8 |
| 1 | S5-03 | 30% trehalose | 2.4 | 3.22 | 94.5 |
| 1 | S5-04 | neat | 1.3 | 4.68 | 94.1 |

Sugars evaluated in this study did not show enhancement of aerosol performance (ED and MMAD) compared to the neat formulation. However, it seems that formulations with sugars provide a better stability profile, for example, when hGH was formulated with a sugar, the soluble aggregate level was lower than the neat formulation; moreover, the sucrose formulation provided the lowest quantity of soluble aggregates.

Example 5

Optimization of Spray Dry Parameters

The objective of this study was to further decrease the MMAD of 4 α-helical bundle protein powders to less than 3 microns without sacrificing dispersibility or increasing protein degradation. Although des-Phe hGH was used, a significant difference was not expected to occur in the characteristics of powders of native full length hGH.

It has been shown (Mumenthaler, M., et al., *Pharm Res.,* 11: 12–20 (1994) and Maa, Y-F, et al. *J. Pharm Sci,* 87: 152–159 (1998)) that aggregation of hgH is inevitable during spray dying and that most of aggregation occurs during the atomization step. The applicants have spray dried neat native hgH into a dry powder at 40 psi atomization (Example 1). The MMAD of this lot of powder was 3.5 microns (VMOD=2.7 microns), larger than 3 microns. The goal of this study was to determine optimized process parameters that would further decrease the aerodynamic particle size to less than 3 microns without sacrificing a low extent of protein aggregation.

One way to achieve reduced MMAD is by reduction in primary particle size, which can be effected by an increase in the atomization pressure or a by a decrease in solids content of the solution to be spray dried. Adjustment of both parameters was explored.

Experimental Design.

Atomization pressure (40–60 psi), and solids content (0.5–2.0% w/v) were used as factors in the design.

The atomizer pressure was increased to 60 psi at 1% solids (S6-02) with the aim of producing smaller particles. The solids content was reduced (S6-03) to 0.5% solids so as to further reduce the particle size. However, it should be noted that at the conditions used to produce smaller particle sizes (lower solids and increased atomization), an increase in aggregation levels of hGH has previously been observed. In other words, increased hGH concentrations may likely result in lower aggregation. Therefore it was decided to increase the solids content to 2%w/v. The aim of experiment S6-04 was to maintain aggregation at its lowest levels employing an atomization pressure of 40 psi. The design matrix is provided below. The starting hGH material was highly impure, as can be seen from the protein purity values in Table 13.

TABLE 12

Experimental Design

| Experiment (No.) | Solids Content (% w/w) | Atomization Pressure (psig) | Remarks (Particle Size/ Aggregation) |
|---|---|---|---|
| S6-01 | 0.5 | 60 | Smallest Particle Greatest Aggregation |
| S6-02 | 1.0 | 60 | Smaller Particle Greater Aggregation |
| S6-03 | 1.0 | 40 | Previously Used |
| S6-04 | 2.0 | 40 | Largest Particle Least Aggregation |

Solution preparation and spray drying was conducted as described in the Examples above. Characterization of the resulting spray dried powders is provided below in tabular form.

TABLE 13

Characterization of Spray Dried Solids

| % solids. atom. pressure | 0.5%, | 60 psi | 1.0%, | 60 psi | 1.0%, | 40 psi | 2.0%, | 40 psi |
|---|---|---|---|---|---|---|---|---|
| ED | 83% | | 77% | | 72% | | 72% | |
| MMAD | 3.4 | | 3.8 | | 4.1 | | 4.3 | |
| FPF | 48% | | 39% | | 33% | | 29% | |
| VMOD | | 2.0 | | 2.2 | | 2.5 | | 3.0 |
| Resid. Moisture | 1.3% | | 1.5% | | 0.9% | | 1.3% | |
| IA (UV) | 0.3% | | 0.1% | | 0.5% | | 0.6% | |
| SA (SEC) | 5.4% | | 4.0% | | 4.1% | | 3.1% | |
| Protein Purity | 64.2% | | 63.8% | | 63.8% | | 64.2% | |

Example 6

Use of Amino Acid Stabilizers

Amino acids were explored as potential stabilizers for 4 α-helical bundle proteins during spray-drying. Based upon a compilation of data, the applicants have discovered certain trends or made observations regarding powder formulations containing amino acids. In general, it was observed that decreasing solubility correlates with decreasing moisture sorption and delayed crystallization (Leu>His>Ala>Gly); increasing Van der Waals volume correlates with increasing Tg (Leu>His>Ala>Gly); increasing surface accumulation factor correlates with increasing hydrophobicity; and decreasing surface tension correlates with decreased MMD and aggregation.

Based on this information, certain amino acids (Leu, Ile, Val, nLeu, Phe, and Trp) were explored as potential spray-drying stabilizers for 4 α-helical bundle proteins. In the hGH-amino acid formulations, the percentage of amino acid was maintained below 30% of the total solid contents. It was thought that a low percentage of amino acid may retard/impede crystallization.

Aqueous amino acid-human growth hormone formulations were prepared as described above. A summary of the formulations is provided in Table 14 below.

TABLE 14

Composition of hGH-Amino Acid formulations

| Formulation | pH | hGH (mg/mL) | Amino Acid Name | Amino Acid (mg/mL) | Buffer (mM) | % of Total Solid hGH | % of Total Solid Amino Acid | % of Total Solid Buffer | Total solid (%) |
|---|---|---|---|---|---|---|---|---|---|
| S7-01 | 7.8 | 9.8 | Leu | 4.60 | 5 | 64.9 | 30.5 | 4.6 | 1.5 |
| S7-02 | 7.8 | 9.8 | Ile | 4.59 | 5 | 65.0 | 30.5 | 4.6 | 1.5 |
| S7-03 | 7.8 | 9.8 | Val | 4.59 | 5 | 64.9 | 30.5 | 4.6 | 1.5 |
| S7-04 | 7.8 | 9.8 | nLeu | 4.59 | 5 | 64.9 | 30.5 | 4.6 | 1.5 |
| S7-05 | 7.8 | 9.8 | Phe | 4.60 | 5 | 64.9 | 30.5 | 4.6 | 1.5 |
| S7-06 | 7.8 | 9.8 | Trp | 4.59 | 5 | 64.9 | 30.5 | 4.6 | 1.5 |
| S7-07 | 7.8 | 9.8 | neat | 0 | 5 | 93.4 | 0.0 | 6.6 | 1.0 |

The formulations were prepared as described in detail in the Examples above utilizing an atomization pressure of 80 psi; powder recovery yields ranged from 55 to 66%.

Powder characterization results are provided in tabular form below.

TABLE 15

Emitted Dose

| Formulation | Desciption | pH | Average of 10 samples ED % | SD | RSD % |
|---|---|---|---|---|---|
| S7-01 | 30% Leu | 7.8 | 73.9 | ±5.6 | 7.6 |
| S7-02 | 30% Ile | 7.8 | 76.3 | ±3.5 | 4.6 |
| S7-03 | 30% Val | 7.8 | 74.5 | ±3.8 | 5.2 |
| S7-04 | 30% nLeu | 7.8 | 76.7 | ±2.2 | 2.9 |
| S7-05 | 30% Phe | 7.8 | 73.5 | ±2.6 | 3.6 |
| S7-06 | 30% Trp | 7.8 | 73.7 | ±4.6 | 6.2 |
| S7-07 | neat | 7.8 | 78.5 | ±2.5 | 3.2 |

EDs for all formulations tested ranged from 73.5% to 78.5%.

TABLE 16

MMAD, FPF, CIE and VMD Results

| Formulation | Desciption | PH | MMAD ($\mu$m) | FPF (%) | VMD ($\mu$m) |
|---|---|---|---|---|---|
| S7-01 | 30% Leu | 7.8 | 3.0 | 56 | 2.0 |
| S7-02 | 30% Ile | 7.8 | 3.1 | 54 | 2.0 |
| S7-03 | 30% Val | 7.8 | 3.4 | 49 | 2.1 |
| S7-04 | 30% nLeu | 7.8 | 3.1 | 56 | 2.0 |
| S7-05 | 30% Phe | 7.8 | 3.2 | 53 | 2.0 |
| S7-06 | 30% Trp | 7.8 | 3.6 | 43 | 2.2 |
| S7-07 | neat | 7.8 | 3.3 | 49 | 1.9 |

Powders from the formulations exhibited MMAD values from 3.0–3.6 microns. Formulations with Trp and Val possessed larger MMAD values of 3.6 and 3.4 microns, respectively. There was no significant difference in MMAD for formulations containing Leu, Ile and nleu. The neat formulation MMAD is 3.3 microns, which is much smaller than the MMAD data of neat formulations from previous Examples. One factor that may have contributed to the difference is the higher atomization pressure (80 psi), since an atomization pressure of 80 psi will favor the formation of small particle sizes over an atomization pressure of 60 psi. The trend of VMD for the formulations was consistent with the MMAD data trend. The particle size distributions for the formulations were similar. It appears Leu, Ile and nleu have slightly better properties as spray drying stabilizers, lending themselves to the formation of particles with small aerodynamic sizes and high FPF.

The residual moisture content of all powders ranged from 0.8 to 1.5%.

TABLE 17

Characterization of chemical degradation by RP-HPLC

| Formulation | Description | pH | Average of 3 injections (%) hGH | SD | % RSD | EE | SD | % RSD |
|---|---|---|---|---|---|---|---|---|
| H051RP | Fresh reconstituted | | 95.7 | 0.4 | 0.4 | 4.3 | 0.4 | 9.1 |
| H051RP | Starting material | | 95.5 | 0.5 | 0.5 | 4.5 | 0.5 | 10.7 |
| H051RP | After diafiltratn | 7.8 | 95.5 | 0.4 | 0.4 | 4.5 | 0.4 | 8.7 |
| S7-01 | 30% Leu | 7.8 | 95.7 | 0.2 | 0.2 | 4.3 | 0.2 | 4.1 |
| S7-02 | 30% Ile | 7.8 | 95.5 | 0.1 | 0.1 | 4.5 | 0.1 | 1.6 |
| S7-03 | 30% Val | 7.8 | 95.4 | 0.1 | 0.1 | 4.6 | 0.1 | 2.2 |
| S7-04 | 30% nLeu | 7.8 | 95.5 | 0.1 | 0.1 | 4.5 | 0.1 | 2.1 |
| S7-05 | 30% Phe | 7.8 | 95.7 | 0.1 | 0.1 | 4.3 | 0.1 | 1.4 |
| S7-06 | 30% Trp | 7.8 | 95.7 | 0.4 | 0.4 | 4.4 | 0.4 | 8.6 |
| S7-07 | neat | 7.8 | 95.3 | 0.2 | 0.2 | 4.7 | 0.2 | 3.2 |

The data indicate the percentages of hGH and early-eluted peaks (EE) were in a similar level for all formulations studied. No significant differences in percentage of hGH and EE between the formulations were observed from the RP-HPLC analysis. Compared to non-spray dried solutions, it appears that there was no increase in early-eluted peaks for any of the formulations.

TABLE 18

Comparison of soluble aggregates (SA) by SE-HPLC

| | | | Average of 3 injections (%) | | | | | | | |
|---|---|---|---|---|---|---|---|---|---|---|
| | | | 1st preparation | | | | 2nd preparation | | | |
| Formulation | Description | pH | hGH | SD | SA | SD | hGH | SD | SA | SD |
| H051RP | Fresh reconstituted | | 99.9 | 0.03 | 0.1 | 0.03 | | | | |
| H051RP | Starting material | | 99.7 | 0.03 | 0.3 | 0.03 | | | | |
| H051RP | After diafiltratn | 7.8 | 99.7 | 0.03 | 0.3 | 0.03 | | | | |
| S7-01 | 30% Leu | 7.8 | 93.9 | 0.16 | 6.1 | 0.16 | 96.3 | 0.15 | 3.8 | 0.15 |
| S7-02 | 30% Ile | 7.8 | 94.7 | 0.15 | 5.3 | 0.15 | 96.7 | 0.20 | 3.3 | 0.20 |
| S7-03 | 30% Val | 7.8 | 95.0 | 0.06 | 5.0 | 0.06 | 97.5 | 0.24 | 2.5 | 0.24 |

TABLE 18-continued

Comparison of soluble aggregates (SA) by SE-HPLC

| Formulation | Description | pH | Average of 3 injections (%) 1st preparation hGH | SD | SA | SD | 2nd preparation hGH | SD | SA | SD |
|---|---|---|---|---|---|---|---|---|---|---|
| S7-04 | 30% nLeu | 7.8 | 96.6 | 0.06 | 3.4 | 0.06 | 99.2 | 0.06 | 0.8 | 0.06 |
| S7-05 | 30% Phe | 7.8 | 96.7 | 0.09 | 3.3 | 0.09 | 98.6 | 0.09 | 1.4 | 0.09 |
| S7-06 | 30% Trp | 7.8 | 96.6 | 0.06 | 3.4 | 0.06 | 99.2 | 0.06 | 0.8 | 0.06 |
| S7-07 | neat | 7.8 | 96.7 | 0.09 | 3.3 | 0.09 | 98.6 | 0.09 | 1.4 | 0.09 |

TABLE 19

Characterization of soluble aggregates (SA) by SE-HPLC

| Formulation | Description | pH | Average of 3 injections (%) hGH | SD | % RSD | EE | SD | % RSD |
|---|---|---|---|---|---|---|---|---|
| S7-01 | 30% Leu | 7.8 | 96.3 | 0.2 | 0.2 | 3.8 | 0.2 | 4.1 |
| S7-02 | 30% Ile | 7.8 | 96.7 | 0.2 | 0.2 | 3.3 | 0.2 | 6.1 |
| S7-03 | 30% Val | 7.8 | 97.5 | 0.2 | 0.3 | 2.5 | 0.2 | 9.7 |
| S7-04 | 30% nLeu | 7.8 | 99.2 | 0.1 | 0.1 | 0.8 | 0.1 | 7.6 |
| S7-05 | 30% Phe | 7.8 | 98.6 | 0.1 | 0.1 | 1.4 | 0.1 | 6.1 |
| S7-06 | 30% Trp | 7.8 | 99.2 | 0.1 | 0.1 | 0.8 | 0.1 | 7.6 |
| S7-07 | neat | 7.8 | 98.6 | 0.1 | 0.1 | 1.4 | 0.1 | 6.1 |

It appeared that formulations with Leu, Ile and Val had higher soluble aggregates while the other formulations had similar level of soluble aggregates (~1%).

TABLE 20

Characterization of insoluble aggregates by UV spectroscopy

| Formulation | Description | pH | Average of 3 scans (%) IA | SD | % RSD |
|---|---|---|---|---|---|
| H051RP | Starting material | | 1.2 | 0.2 | 13.8 |
| H051RP | After diafiltratn | 7.8 | 1.6 | 0.2 | 14.7 |
| S7-01 | 30% Leu | 7.8 | 1.1 | 0.0 | 4.1 |
| S7-02 | 30% Ile | 7.8 | 0.9 | 0.1 | 14.0 |
| S7-03 | 30% Val | 7.8 | 1.5 | 0.2 | 12.2 |
| S7-04 | 30% nLeu | 7.8 | 1.2 | 0.5 | 37.6 |
| S7-05 | 30% Phe | 7.8 | 0.8 | 0.1 | 11.6 |
| S7-06 | 30% Trp | 7.8 | 1.5 | 0.3 | 22.7 |
| S7-07 | neat | 7.8 | 0.3 | 0.1 | 42.0 |

The insoluble aggregates were in a range of 0.3 to 1.5% for all formulations tested.

It was observed that the IA did not increase after the spray drying. All formulations had similar levels of IA. The SD and %RSD reported in the Table 11 were obtained from the triple scans of the same samples.

TABLE 21

Calculation of total monomer percentage

| Formulation | Description | PH | (%) IA | SA | TM |
|---|---|---|---|---|---|
| S7-01 | 30% Leu | 7.8 | 1.1 | 3.8 | 95.2 |
| S7-02 | 30% Ile | 7.8 | 0.9 | 3.3 | 95.8 |
| S7-03 | 30% Val | 7.8 | 1.5 | 2.5 | 96.1 |
| S7-04 | 30% nLeu | 7.8 | 1.2 | 0.8 | 98.0 |
| S7-05 | 30% Phe | 7.8 | 0.8 | 1.4 | 97.8 |
| S7-06 | 30% Trp | 7.8 | 1.5 | 0.8 | 97.7 |
| S7-07 | neat | 7.8 | 0.3 | 1.4 | 98.3 |

In summary, the EDs of all formulations were above 73% and MMADs ranged from about 3.0 to 3.6 μm. Powders formulated with Val and Trp possessed relatively large MMADs (3.4 and 3.6 μm), while from a chemical stability point of view, hGH formulated with each Leu and Ile at a 30% level had slightly higher soluble aggregates than did formulations containing the other amino acids.

Example 7

Spray Dried Compositions of hGH

Four formulations of des-phe hGH were prepared and spray dried as described generally above: a neat hGH formulation, a $Zn^{2+}$/Tween20/hGH formulation, and two different zinc containing formulations, $Zn^{2+}$:hGH (7:1 and 20:1). Protein concentrations were adjusted by the addition of 5 mM sodium phosphate buffer. Batch sizes ranged from 500 mg to 550 mg, and the powder yields ranged from 80% to 100%. A summary of formulation related data is provided in the table below.

TABLE 22 hGH Formulation Compositions

| Exp. No. | [hGH], mg/ml | Tween 20, % | Zn:hGH Molar ratio | pH |
|---|---|---|---|---|
| 1276-52 | 9.7 | 0 | 0 | 7.7 |
| 1276-53 | 9.5 | 0.05 | 2:1 | 7.5 |
| 1276-54 | 8.6 | 0 | 20:1 | 5.4 |
| 1381-72 | 9.7 | 0 | 0 | 7.7 |
| 1381-86 | 9.3 | 0 | 7:1 | 7.7 |

The physical and chemical stability and aerosol performance of the spray dried powders was determined and is summarized below.

TABLE 23

| Characterization of Spray-Dried hGH Powders | | | | | | |
|---|---|---|---|---|---|---|
| Exp. No. | Time point | Moisture content, % wt | MMAD, μm | ED, % | Insol. Aggregates, % | Soluble Aggregates, % |
| 1276-52 | initial | 2.6 | 4.5 | 65 | | |
| 1276-53 | initial | 2.5 | 3.9 | 49 | 1.3 | 5.5 |
| 1276-54 | initial | 2.1 | 3.5 | 75 | 2.6 | 4.4 |
| 1381-72 | initial | 2.9 | 3.6 | 73 | 1.2 | 4.2 |
| 1381-72 | 3 wk, 25° C./60 RH-wrapped blister packs | 2.0 | 3.5 | 70 | 1.1 | 6.7 |
| 1381-72 | 3 wk, 40° C./75 RH-wrapped blister packs | 1.9 | 3.4 | 69 | 1.3 | 8.2 |
| 1381-86 | initial | 2.4 | 3.2 | 69 | | |

Following a month's storage under both ambient and accelerated environmental conditions, both the emitted dose and MMAD for the neat powder remained approximately constant at 70% and 3.5 μm respectively, demonstrating the robustness of the neat formulation.

Example 8 hGH Atomization Study

The following studies were undertaken to determine the effects of formulation and/or processing parameters such as optimized atomization pressures for spray drying a representative 4-α helix protein, hGH, when combined with certain amounts of stabilizing excipients. The atomization studies were carried out on a Buchi 190 as described previously and atomized solutions were collected in an Erlenmeyer flask. All experiments were performed at a constant concentration of 10 mg/mL of met-rHGH in 5 mM phosphate buffer and atomized at 80 psi unless otherwise indicated. The excipients/solvents investigated were alpha glycerol phosphate, leucine, ethanol, trileucine, triphenylalanine, F-68, rHA, zinc, magnesium, calcium, and hydroxyethylstarch at the amounts indicated in Table 24 below. All pre and post atomized samples were assayed by pH, UV and SE-HPLC. Aliquots of samples were also centrifuged and analyzed by UV. All pre-atomized samples were measured for surface tension.

TABLE 24

| Formulation Components | | | |
|---|---|---|---|
| Excipient | Excipient amount | hGH amount | 5 mM phos. buffer |
| 10% Agphos | 6 mg | 2.158 ml | 3.842 ml |
| 30% Agphos | 18 mg | 2.158 ml | 3.842 ml |
| 30% Leu | 18 mg | 2.158 ml | 3.842 ml |
| 5% Ethanol | 300 μl | 2.158 ml | 3.542 ml |
| 30% Ethanol | 1.8 ml | 2.158 ml | 2.042 ml |
| 5% Trileucine | 2.93 mg | 2.158 ml | 3.842 ml |
| 30% Trileucine | 17.91 mg | 2.158 ml | 3.842 ml |
| 30% Phe-3 | 18.03 mg | 1.813 ml | 4.187 ml |
| 70% Phe-3 | 42.14 mg | 1.813 ml | 4.187 ml |
| 0.01% F-68 | 6 μl | 1.813 ml | 4.181 ml |
| 0.1% F-68 | 60 μl | 1.813 ml | 4.127 ml |

TABLE 24-continued

| Formulation Components | | | |
|---|---|---|---|
| 5% rHA | 0.012 ml | 1.813 ml | 4.175 ml |
| 50% rHA | 0.120 ml | 1.813 ml | 4.067 ml |
| Zn 2:1 | 17 μl | 2.406 ml | 3.577 ml |
| Zn 7:1 | 58 μl | 2.406 ml | 3.536 ml |
| Zn 20:1 | 166 μl | 2.406 ml | 3.428 ml |
| Mg 20:1 | 190 μl | 2.406 ml | 3.404 ml |
| Ca 20:1 | 223 μl | 2.406 ml | 3.371 ml |
| 20% HES | 11.97 mg | 2.406 ml | 3.594 ml |
| 50% HES | 30.1 mg | 2.406 ml | 3.594 ml |

| | SE-HPLC | | | | UV | | |
|---|---|---|---|---|---|---|---|
| | % Monomer | | mean | wrt pre | % Insol Agg (unspun) | % Insol Agg (spun) | pH |
| 40 psi | 95.59 | 95.44 | 95.52 | 96.05 | 4.0 | 1.9 | 7.4 |
| 60 psi | 94.88 | 94.87 | 94.88 | 95.40 | 4.1 | 1.8 | 7.2 |
| 80 psi | 94.8 | 94.8 | 94.80 | 95.33 | 3.3 | 2.1 | 7.3 |
| pre 10/3.6 | 86.69 | 89.22 | 87.96 | | 2.1 | 6.3 | 6.8 |
| (6.8) post | 85.37 | 85.33 | 85.35 | 98.48 | 7.2 | 1.5 | 6.84 |
| pre 10/7.5 | 75.17 | 75.96 | 75.57 | | 3.2 | 1.5 | 7.46 |
| post | 67.86 | 67.49 | 67.68 | 90.28 | 3.5 | 3.2 | 7.46 |
| pre 2/7.5 | 83.06 | 81.76 | 82.41 | | 3.5 | 0.1 | 7.48 |
| post | 61.45 | 61.61 | 61.53 | 73.98 | 4.1 | 4.2 | 7.41 |
| pre 10/3.6 | 86.81 | | | | 0.7 | 0.9 | 3.52 |
| post | 82.52 | | | 95.06 | 1.3 | 1.2 | 3.51 |
| pre 10% | 84.98 | | | | 1.1 | 5.5 | 7.27 |
| agphos post | 75.55 | | | 88.90 | 3.9 | 7.8 | 7.18 |
| pre 30% | 84.02 | | | | 3.0 | 6.0 | 7.37 |
| agphos post | 76.13 | | | 90.61 | 6.0 | 7.8 | 7.25 |
| pre 30% | 85.36 | | | | 1.9 | 4.8 | 7.3 |
| leu-3 post | 75.17 | | | 88.06 | 4.6 | 3.2 | 7.16 |
| pre 5% | 85.41 | | | | 1.2 | 1.9 | 7.44 |
| etoh post | 76.77 | | | 89.88 | 2.7 | 4.3 | 7.29 |
| pre 30% | 79.46 | | | | 9.9 | 1.2 | 6.97 |
| etoh post | 78.84 | | | 99.22 | 12.8 | 0.7 | 6.8 |
| pre 5% | 85.82 | | | | 2.5 | 2.1 | 7.31 |
| leu-3 post | 77.19 | | | 89.94 | 2.4 | 8.2 | 7.19 |
| pre 30% | 86.02 | | | | 2.8 | 4.2 | 7.15 |
| leu-3 post | 82.1 | | | 95.44 | 5.6 | 2.2 | 7.04 |
| pre 30% | 99.36 | | | | 1.5% | 0.5% | 7.44 |
| Ile-3 post | 98.6 | | | 99.24 | 0.9% | 0.4% | 7.37 |
| pre 70% | 99.34 | | | | 0.4% | 0.3% | 7.64 |
| Ile-3 post | 98.89 | | | 99.55 | 0.6% | 0.6% | 7.6 |
| pre 30% | 99.16 | | | | 2.2% | 0.9% | 9.17 |
| Phe-3 post | 98.12 | | | 98.95 | 1.7% | 0.4% | 8.82 |
| pre 70% | 97.74 | | | | 3.1% | 1.1% | 10.64 |
| Phe-3 post | 97.68 | | | 99.94 | 2.8% | 1.2% | 10.49 |
| pre 0.01% | 99.32 | | | | 0.2% | 0.6% | 7.2 |
| F-68 post | 93.06 | | | 93.70 | 6.3% | 4.3% | 7.08 |
| pre 0.1% | 99.27 | | | | −0.5% | 0.6% | 7.39 |
| F-68 post | 97.37 | | | 98.09 | 4.4% | 3.2% | 7.04 |
| pre 5% | 92.87 | | | | −0.6% | 1.6% | 7.4 |
| rHA post | 85.73 | | | 92.31 | 0.8% | 0.8% | 7.11 |
| pre 50% | 66.24 | | | | 0.2% | 1.4% | 7.28 |
| rHA post | 61.88 | | | 93.42 | 7.4% | 3.0% | 7.04 |
| pre Zn | 97.53 | | | | 7.1% | 4.7% | 3.04 |
| 2:1 post | 95.59 | | | 98.01 | 23.7% | 0.3% | 3.05 |
| pre Zn | 97.83 | | | | 16.4% | 0.8% | 3.43 |
| 7:1 post | 96.51 | | | 98.65 | 52.4% | 1.0% | 3.44 |
| pre Zn | 99.04 | | | | 49.7% | 5.4% | 3.31 |
| 20:1 post | 93.09 | | | 93.99 | 57.8% | 2.6% | 3.2 |
| pre Mg | 97.77 | | | | 9.7% | 1.4% | 3.39 |
| 20:1 post | 95.59 | | | 97.77 | 26.5% | 0.7% | 3.43 |
| pre Ca | 97.79 | | | | 8.6% | 0.2% | 3.16 |
| 20:1 post | 96.08 | | | 98.25 | 37.2% | 1.0% | 3.21 |
| pre 20% | 98.07 | | | | 3.9% | 0.7% | 7.21 |
| HES post | 95.03 | | | 96.90 | 4.1% | 1.6% | 7.16 |
| pre 50% | 98.2 | | | | 3.1% | 1.3% | 7.28 |
| HES post | 93.64 | | | 95.36 | 4.2% | 3.0% | 7.28 |

In looking at the results in the table above, and comparing the post spray dried values to the pre-spray dried values, the agphos formulation showed a slight decrease in aggregation when agphos was present at the higher concentration; the leucine-containing formulation did not perform as well, but had good results overall. The ethanol-containing formulations showed a decrease in aggregation, particularly at the higher concentration, although precipitate did fall out of solution, especially at the higher concentration. The trileucine formulation showed a decrease in aggregation at the higher concentration, while there was no change in aggregation for the low and high concentration Phe-3 formulations—both performed well. The F-68 containing formulation exhibited a decrease in aggregation at the higher concentration, while for the zinc-containing formulations, the zinc 7:1 formulation performed the best. (For all of the zinc formulations, precipitate fell out of the solution, with the worst being the 20:1.) Formulations containing the cations, Mg and Ca, also performed well, but similarly experienced precipitate formation. (note: problem with ppt falling out of solution). The HES-containing formulation showed a slight increase in aggregation at the higher HES concentration.

It is claimed:

1. A spray-dried, inhaleable 4-α-helix bundle protein powder having superior aerosolizability and protein stability, comprising a 4-α helix bundle protein, wherein said powder is free from surfactant and characterized by (i) an emitted dose of at least about 65%, and (ii) a total protein aggregate content of less than 10%.

2. The powder of claim 1, wherein said 4-α helix bundle protein comprises growth hormone.

3. The powder of claim 2, wherein said growth hormone is human growth hormone.

4. The powder of claim 3 consisting essentially of human growth hormone and buffer.

5. The powder of claim 4 consisting essentially of human growth hormone and phosphate buffer.

6. The powder of claim 4 further characterized by an MMAD of less than about 3.5 microns.

7. The powder of claim 1, further comprising a stabilizing excipient, which when employed during spray-drying in combination with said 4-α helix bundle protein, is effective to maintain or lower the aggregate level of the powder in comparison to the corresponding neat formulation.

8. The powder of claim 7, wherein said excipient is selected from the group consisting of sugars, amino acids and oligomers comprising 2–5 amino acids.

9. The powder of claim 7, wherein said powder is rapid-acting.

10. The powder of claim 7, which is water-soluble.

11. The powder of claim 8, wherein said excipient is a sugar.

12. The powder of claim 11, wherein the sugar is sucrose or raffinose.

13. The powder of claim 12, wherein the protein is human growth hormone.

14. The powder of claim 8, wherein said excipient is an amino acid.

15. The powder of claim 14, wherein said amino acid is selected from the group consisting of asparagine, isoleucine, phenylalanine, tryptophan, tyrosine, leucine, norleucine and valine.

16. The powder of claim 15, wherein said amino acid is selected from the group consisting of leucine, isoleucine, and norleucine.

17. The powder of claim 15, wherein said protein is human growth hormone.

18. The powder of claim 8, wherein said excipient is an oligomer comprising 2–5 amino acids.

19. The powder of claim 18, wherein said excipient is trileucine.

20. The powder of claim 19, wherein said protein is human growth hormone.

21. The powder of claim 20, characterized by an MMAD of less than 3.0 microns.

22. The powder of claim 7, comprising less than about 30 percent by weight of said stabilizing excipient.

23. The powder of claim 7, further characterized by a total aggregate content of less than about 10% after storage for one month at 40° C.

24. The powder of claim 7, comprising at least about 50% by weight 4-a helix bundle protein.

25. A method for preparing an inhaleable 4-α helix bundle protein powder having superior aerosolizability and protein stability upon spray drying, said method comprising:

(a) dissolving a 4-alpha helix bundle protein in an aqueous solvent in the absence of surfactant to form a solution, and (b) spray drying said solution under conditions effective to produce a powder characterized by (i) an emitted dose of at least about 65%, and (ii) a total protein aggregate content of less than 10%.

26. The method of claim 25, wherein said 4-α helix bundle protein comprises growth hormone.

27. The powder of claim 26, wherein said growth hormone is human growth hormone.

28. The method of claim 25, wherein the solution formed in step (a) has a solids content ranging from about 0.02 to about 20% by weight.

29. The method of claim 28, wherein the solution formed in step (a) has a solids content ranging from about 0.05 to about 5% by weight.

30. The method of claim 28, wherein the solution formed in step (a) has a solids content ranging from about 0.05 to about 2% by weight.

31. The method of claim 25, wherein the solution formed in step (a) consists essentially of a 4-α helix bundle protein and a buffer.

32. The method of claim 31, wherein said buffer is phosphate.

33. The method of claim 31, wherein said protein comprises growth hormone.

34. The method of claim 25, wherein the powder produced in step (b) has an MMAD of less than about 3.5 microns.

35. The method of claim 25, further comprising adding to the protein solution formed in step (a) a stabilizing excipient effective to maintain or lower the aggregate level of the powder in comparison to the neat formulation.

36. The method of claim 35, wherein the stabilizing excipient is selected from the group consisting of sugars, amino acids and oligomers comprising 2–5 amino acids.

37. The method of claim 36, wherein the stabilizing excipient is a sugar.

38. The method of claim 37, wherein the sugar is sucrose or raffinose.

39. The method of claim 38, wherein the protein is human growth hormone.

40. The method of claim 36, wherein the excipient is an amino acid.

41. The method of claim 40, wherein the amino acid is selected from the group consisting of asparagine, isoleucine, phenylalanine, tryptophan, tyrosine, leucine, norleucine and valine.

42. The method of claim 41, wherein said amino acid is selected from the group consisting of leucine, isoleucine, and norleucine.

43. The method of claim 42, wherein said protein is human growth hormone.

44. The method of claim 36, wherein said excipient is an oligomer comprising 2–5 amino acids.

45. The method of claim 44, wherein said excipient is trileucine.

46. The method of claim 45, wherein said protein is human growth hormone.

47. The method of claim 46, wherein the powder produced in step (b) is further characterized by an MMAD of less than 3.0

48. The method of claim 45, further comprising in step (a), adjusting the pH of the protein solution to less than about 4.

49. The method of claim 25, wherein the 4-α helix bundle protein dissolved in said aqueous solvent comprises at least about 50% by weight of the total solids present in said solution.

50. The method of claim 25, wherein said conditions comprise spray drying said solution at atomization pressures in a range from about 30–100 psi.

51. The method of claim 50, wherein said conditions comprise spray drying said solution at atomization pressures in a range from about 30–80 psi.

52. A spray-dried, inhaleable human growth hormone powder having superior aerosolizability and protein stability, comprising human growth hormone, wherein said powder is free from surfactant and characterized by (i) an emitted dose of at least about 65%, and (ii) a total protein aggregate content of less than 10%.

* * * * *